(12) United States Patent
Knobbe et al.

(10) Patent No.: US 6,575,905 B2
(45) Date of Patent: Jun. 10, 2003

(54) METHOD AND APPARATUS FOR REAL-TIME ESTIMATION OF PHYSIOLOGICAL PARAMETERS

(75) Inventors: Edward J. Knobbe, Fallbrook, CA (US); Wah L. Lim, Newport Beach, CA (US); Bruce A. Buckingham, Palo Alto, CA (US)

(73) Assignee: Knobbe, Lim & Buckingham, Newport Beach, CA (US)

( * ) Notice: Subject to any disclaimer, the term of this patent is extended or adjusted under 35 U.S.C. 154(b) by 27 days.

(21) Appl. No.: 09/960,846

(22) Filed: Sep. 21, 2001

(65) Prior Publication Data

US 2002/0099282 A1 Jul. 25, 2002

Related U.S. Application Data

(60) Provisional application No. 60/234,632, filed on Sep. 22, 2000.

(51) Int. Cl.[7] .............................. A61B 5/00; A61B 10/00
(52) U.S. Cl. ........................ 600/365; 128/923; 128/924
(58) Field of Search ................................ 600/365, 347, 600/345, 316, 309; 128/923, 924, 925

(56) References Cited

U.S. PATENT DOCUMENTS

| | | | |
|---|---|---|---|
| 4,655,225 A | 4/1987 | Dähne et al. | |
| 5,070,874 A | 12/1991 | Barnes et al. | |
| 5,086,229 A | 2/1992 | Rosenthal et al. | |
| 5,218,553 A | * 6/1993 | de Loos-Vollebregt et al. | 702/23 |
| 5,298,022 A | 3/1994 | Bernardi | |
| 5,308,982 A | * 5/1994 | Ivaldi et al. | 250/339.12 |
| 5,494,032 A | 2/1996 | Robinson et al. | |
| 5,497,772 A | 3/1996 | Schulman et al. | |
| 5,685,299 A | 11/1997 | Diab et al. | |
| 5,995,860 A | 11/1999 | Sun et al. | |
| 6,023,009 A | 2/2000 | Stegemann et al. | |
| 6,036,642 A | 3/2000 | Diab et al. | |
| 6,061,582 A | 5/2000 | Small et al. | |
| 6,081,735 A | 6/2000 | Diab et al. | |
| 6,083,172 A | 7/2000 | Baker, Jr. et al. | |
| 6,152,876 A | 11/2000 | Robinson et al. | |
| 6,236,872 B1 | 5/2001 | Diab et al. | |
| 6,263,222 B1 | 7/2001 | Diab et al. | |
| 6,272,480 B1 | 8/2001 | Tresp et al. | |
| 6,368,272 B1 | * 4/2002 | Porumbescu | 600/300 |

OTHER PUBLICATIONS

U.S. patent application Ser. No. 09/960,855, Knobbe et al., filed Sep. 21, 2001.

A. Gelb, *Applied Optimal Estimation*, pp. 188–189, M.I.T. Press, Cambridge, Mass., 1974.

E.J. Knobbe, "Optimal Control of Linear Stochastic systems with Process and Observation Time Delays", Control and Dynamic Systems, vol. 31, pp. 185–192, Academic Press, Inc., 1989.

(List continued on next page.)

*Primary Examiner*—Max F. Hindenburg
*Assistant Examiner*—Navin Natnithithadha
(74) *Attorney, Agent, or Firm*—Knobbe, Martens, Olson & Bear LLP

(57) ABSTRACT

A real-time glucose estimator uses a linearized Kalman filter to determine a best estimate of glucose level in real time. The real-time glucose estimator receives at least one measurement corresponding to glucose level. The measurement can be obtained with one or more sensors and is provided to the linearized Kalman filter in real time. The linearized Kalman filter has dynamic models and executes a recursive routine to determine the best estimate of glucose level based upon the measurement. Additional information can be provided to the linearized Kalman filter for initialization, configuration, and the like. Outputs of the linearized Kalman filter can be provided to a patient health monitor for display or for statistical testing to determine status of the real-time glucose estimator. The real-time glucose estimator can be implemented using a software algorithm.

34 Claims, 21 Drawing Sheets

OTHER PUBLICATIONS

Fast On–Line Data Evaluation of Flow–Injection Analysis Signals Based On Parameter Estimation By An Extended Kalman Filter, by X. Wu, K.–H. Bellgardt, Institute für Technische Chemie, Universität Hannover, Callinstr. 3,30167 Hannover, Germany, Journal of Biotechnology, 62 (1998), pp. 11–28.

The Closed–Loop Regulation of Blood Glucose In Diabetics, by E.A. Woodruff, S. Gulaya, and R.B. Northrop, The University of Connecticut, Electrical & Systems Engineering Department, U–157, Engineering III, 260 Glenbrook Road, Storrs, Connecticut 06268, 1988 IEEE, pp. 54–57.

Model Predictive Control For Infusion Pump Insulin Delivery, by R.S. Parker, F.J. Doyle II, J.E. Hartin, and N.A. Peppas, School of Chemical Engineering, Purdue University, West Lafayette, IN 47907–1283, IEEE pp. 1882–1883.

* cited by examiner

INITIALIZATION

| | EXAMPLE EMBODIMENT | |
|---|---|---|
| | BEFORE 20 HOURS | AFTER 20 HOURS |
| • STATE VECTOR $X_e(0) = X_{e0}$ | $\begin{bmatrix} g_e(0) \\ S_e(0) \end{bmatrix} = \begin{bmatrix} 150 \\ 0.25 \end{bmatrix}$ | N. A. |
| • PROCESS FUNCTION $dX_e(0) = f(X_e(0))$ | $\begin{bmatrix} dg_e(0) \\ dS_e(0) \end{bmatrix} = \begin{bmatrix} 0.0 \\ 0.0 \end{bmatrix}$ | $\begin{bmatrix} dg_e(0) \\ dS_e(0) \end{bmatrix} = \begin{bmatrix} 0.0 \\ -\alpha * S_e(0) \end{bmatrix}$ |
| • COVARIANCE MATRIX $P(0) = P_0$ | $\begin{bmatrix} 15^2 & 0 \\ 0 & 0.02^2 \end{bmatrix}$ | N. A. |
| • PROCESS NOISE MATRIX $Q(0) = Q$ | $\begin{bmatrix} 20^2 & 0 \\ 0 & 0.0002^2 \end{bmatrix}$ | $\begin{bmatrix} 20^2 & 0 \\ 0 & 0.0002^2 \end{bmatrix}$ |
| • MEASUREMENT NOISE MATRIX $R(0) = R$ | $\dfrac{CBG \quad SENSOR}{15^2 \quad\quad 5^2}$ | $\dfrac{CBG \quad SENSOR}{15^2 \quad\quad 5^2}$ |

NOTE: $\alpha = 0.012$ FOR A 5 MINUTE CYCLE TIME

→ TO TIME UPDATE

SENSOR & CBG MEASUREMENTS $\longrightarrow Y_m$

FROM TIME UPDATE $\longrightarrow$

MEASUREMENT UPDATE

- KALMAN GAIN
$$K(i) = P^-(i)H(i)[h(i)P^-(i)H^T(i)+R(i)]^{-1}$$

- ESTIMATED MEASUREMENT ERROR (RESIDUAL)
$$y(i) = Y_m(i) - Y_e(i)$$

- STATE VECTOR
$$X_e^+(i) = X_e^-(i) + K(i)*y(i)$$

- COVARIANCE MATRIX
$$P^+(i) = [I - K(i)H(i)]P^-(i)$$

EXAMPLE EMBODIMENT

| BEFORE 20 HOURS | AFTER 20 HOURS |
|---|---|
| MATRICES DEFINED IN FIG. 3C | PROBE SENSOR $y_s(i) = [S(i)*g(i)+\xi_s^*(i)] - S_e^-(i)*g_e^-(i)$ |
|  | CBG MEAS. $y_g(i) = [g(i)+\xi_g^*(i)] - g_e^-(i)$ |
| AS DEFINED | AS DEFINED |

* $\xi_s$ & $\xi_g$ DENOTE SENSOR & CBG MEASUREMENT ERRORS, RESPECTIVELY, AND MODELED BY THE VARIANCE, R $\longrightarrow$ TO TIME UPDATE $y(i)$, $P^+(i)$, $H(i)$, $R(i)$ FROM MEASUREMENT UPDATE

- SUM OF RESIDUALS; $Sy(i) = \sum\limits^{i} y(i)$ $Sy(i) = Sy(i-1) + y(i)$

- ABSOLUTE VALUE OF SUM OF RESIDUALS; $ASy(i)$ $ASy(i) = \sqrt{Sy^2(i)}$

- RESIDUAL VARIANCE; $Var(y(i))$ $Var(y(i)) = H(i)P(i)H^T(i) + R$

- VARIANCE OF SUM OF RESIDUALS; $Var(Sy(i)) = \sum\limits^{i} Var(y(j)) = SV(i)$ $Var(Sy(i)) = SV(i) = SV(i-1) + Var(y(i))$ ; FOR OPTIMAL EST.

- STANDARD DEVIATION OF $SV(i)$; $STDSV(i)$ $STDSV(i) = \sqrt{SV(i)}$

NOTE: TEST DATA FOR EXAMPLE EMBODIMENT GENERATED USING RESPECTIVE $y(i)$s

FIG. 6B

RESIDUAL TEST DATA

- TIME HISTORY PLOTS/DISPLAY
  - ABSOLUTE VALUE OF RESIDUAL $V_S$ STD OF RESIDUAL
  - ABSOLUTE VALUE OF THE SUM OF THE RESIDUALS

- HYPOTHESIS TESTS; TIME HISTORY OR DISCRETE OUTPUT
  - HYPOTHESIS I : ESTIMATOR PERFORMANCE ACCEPTABLE
  - HYPOTHESIS II : ESTIMATOR PERFORMANCE UNACCEPTABLE

- CONFIDENCE INTERVAL TEST; TIME HISTORY OR DISCRETE OUTPUT
  - PERFORMANCE WITHIN SPECIFIED INTERVAL

- LIKELIHOOD RATIO TEST

→ HEALTH MONITOR INPUT/OUTPUT

○ DYNAMIC PROCESSES MODEL $$\begin{bmatrix} dg_e \\ dS_e \\ dD_e \end{bmatrix} = \begin{bmatrix} -\alpha_g & 0 & B_g \\ 0 & -\alpha_s & 0 \\ 0 & 0 & -\alpha_D \end{bmatrix} \begin{bmatrix} g_e \\ S_e \\ D_e \end{bmatrix} + \begin{bmatrix} B_D \\ 0 \\ 0 \end{bmatrix} u$$

○ TRANSITION MATRIX $$A = \begin{bmatrix} a_{11} & a_{12} & a_{13} \\ a_{21} & a_{22} & a_{23} \\ a_{31} & a_{32} & a_{33} \end{bmatrix} \; ; \quad \begin{aligned} a_{11} &= e^{-\alpha_g \Delta t} \; ; \; a_{13} = \left(\frac{B_g}{\alpha_g - \alpha_I}\right)\left(e^{-\alpha_I \Delta t} - e^{-\alpha_g \Delta t}\right) \\ a_{22} &= \begin{cases} 1 & \text{for } T < 20 \text{ hrs} \\ e^{-\alpha_s \Delta t} & \text{for } T \geq 20 \text{ hrs} \end{cases} ; \; a_{33} = e^{-\alpha_D \Delta t} \\ a_{12} &= a_{21} = a_{23} = a_{31} = a_{32} = 0 \end{aligned}$$

○ CONTROLLED ERROR: $g_c = DX_e - g_T = (g_e - g_T) \rightarrow D = [1 \; 0 \; 0]$ ○ CONTROLLER COMMAND: $B_D u \rightarrow B = [B_D \; 0 \; 0]^T$ ○ MEASUREMENTS: $H_1 = [S_e \; g_e \; 0]$ & $H_2 = [1 \; 0 \; 0]$ ○ COSTS: CONTROLLED ERROR; $g_c$ ; COST; $C_g$
CONTROL COMMAND, $u$ ; COST; $C_u$ $\Bigg\}$ COST FUNCTION: $E\left\{\sum_{j=1}^{i}\left[C_g^2 \, g_c^2(i) + C_u^2 \, u^2(i)\right]\right\}$

- CONTROL GAIN COMPUTATION, $K_c(C_g, e_u)$ $K_c(i)$ : TIME VARYING, COMPUTATIONALLY INTENSIVE $K_{css}$ : STEADY STATE, PRE-COMPUTED

- PUMP CONTROL COMMAND:

$u(i) = -K_c(g_e(i) - g_T)$

- CLOSED LOOP CONTROL: $X_e^-(i+1) = A(i)X_e^+(i) + Bu(i)$ $$\begin{bmatrix} g_e(i+1) \\ S_e(i+1) \\ D_e(i+1) \end{bmatrix} = \begin{bmatrix} a_{11} & 0 & a_{13} \\ 0 & a_{22} & 0 \\ 0 & 0 & a_{33} \end{bmatrix} \begin{bmatrix} g_e(i) \\ S_e(i) \\ D_e(i) \end{bmatrix} + \begin{bmatrix} B_D \\ 0 \\ 0 \end{bmatrix} u(i)$$

FIG. 9C

METHOD AND APPARATUS FOR REAL-TIME ESTIMATION OF PHYSIOLOGICAL PARAMETERS

PRIORITY CLAIM

The benefit under 35 U.S.C. §119(e) of U.S. Provisional Application No. 60/234,632, filed Sep. 22, 2000, and entitled "REAL TIME ESTIMATION & CONTROL OF BIOLOGICAL PROCESS" is hereby claimed.

COPYRIGHT RIGHTS

A portion of the disclosure of this patent document contains material that is subject to copyright protection. The copyright owner has no objection to the facsimile reproduction by anyone of the patent document or of the patent disclosure as it appears in the Patent and Trademark Office patent files or records, but otherwise reserves all copyright rights whatsoever.

BACKGROUND OF THE INVENTION

1. Field of the Invention

This present invention relates generally to a method and apparatus for estimating physiological parameters and more particularly to an optimal estimator for estimating glucose levels in a patient.

2. Description of the Related Art

Different types of sensors (e.g., optical sensors) are available for monitoring of physiological parameters (e.g., glucose concentration). Glucose monitoring is typically performed by people with diabetes mellitus which is a medical condition involving a body's inability to produce the quantity or quality of insulin needed to maintain a normal circulating blood glucose. Frequent monitoring of glucose is generally necessary to provide effective treatment and to prevent long term complications of diabetes (e.g., blindness, kidney failure, heart failure, etc.). New methods of monitoring glucose are fast, painless and convenient alternatives to the typical capillary blood glucose (CBG) measurements which involve finger pricks that are painful, inconvenient and difficult to perform for long term.

Optical measurement of glucose is performed by focusing a beam of light onto the body. Optical sensors determine glucose concentration by analyzing optical signal changes in wavelength, polarization or intensity of light. However, many factors other than glucose concentration also contribute to the optical signal changes. For example, sensor characteristics (e.g., aging), environmental variations (e.g., changes in temperature, humidity, skin hydration, pH, etc.), and physiological variations (e.g., changes in tissue fluid due to activity, diet, medication or hormone fluctuations) affect sensor measurements.

Various methods are used to improve the accuracy of the sensor measurements. One method (e.g., multivariate spectral analysis) utilizes calibration models developed by initially measuring known glucose concentrations to correct subsequent sensor measurements. The calibration models become inaccurate over time due to dynamic changes in physiological processes. Another method (e.g., adaptive noise canceling) utilizes signal processing to cancel portions of the sensor measurements unrelated to glucose concentration. For example, two substantially simultaneous sensor measurements at different wavelengths make up a composite signal which can be processed to cancel its unknown and erratic portions. However, many sensors do not provide substantially simultaneous measurements at two different wavelengths.

SUMMARY OF THE INVENTION

The present invention solves these and other problems by providing a method and apparatus for making optimal estimates of a physiological parameter (e.g., glucose level), assessing reliability of the optimal estimates, and/or providing optimal control of the physiological parameter in real time using one or more sensor measurements at each measurement time epoch (or interval). The sensor measurements can be time-based (e.g., every five minutes) to provide continuous monitoring and/or regulation of the physiological parameter. The sensor measurements are a function of the physiological parameter within specified uncertainties.

An optimal estimator provides an accurate estimate of glucose level in real time using a sensor with at least one output. In one embodiment, the optimal estimator is integrated with the sensor and an output display to be a compact glucose monitoring device which can be worn by a patient for continuous monitoring and real-time display of glucose level. In an alternate embodiment, the optimal estimator is a separate unit which can interface with different types of sensors and provide one or more outputs for display, further processing by another device, or storage on a memory device.

In one embodiment, the optimal estimator employs a priori deterministic dynamic models developed with stochastic variables and uncertain parameters to make estimates of glucose level. For example, glucose level is defined as one of the stochastic (or random) variables. Dynamic mathematical models define process propagation (i.e., how physiological and sensor parameters change in time) and measurement relationship (i.e., how physiological and sensor parameters relate to environmental conditions). Environmental conditions (e.g., temperature, humidity, pH, patient activity, etc.) can be provided to the optimal estimator intermittently or periodically via environment sensors and/ or data entries by a patient or a doctor.

The optimal estimator uses dynamic models to propagate estimates of respective stochastic variables, error variances, and error covariances forward in time. At each measurement time epoch, the optimal estimator generates real-time estimates of the stochastic variables using one or more sensor outputs and any ancillary input related to environmental conditions. In one embodiment, the optimal estimator employs a linearized Kalman filter to perform optimal estimation of the stochastic variables (e.g., glucose level). In particular, an extended Kalman filter is used to accommodate nonlinear stochastic models.

Before making real-time estimates, the optimal estimator is initialized by providing initial values for the stochastic variables, error variances, and error covariances. For example, a CBG measurement or another direct glucose measurement is performed at initialization to provide a starting value for the stochastic variable corresponding to glucose level.

In one embodiment, the optimal estimator provides one or more outputs to a patient health monitor which is capable of optimized real-time decisions and displays. The patient health monitor evaluates system performance by assessing the performance of the sensor and/or optimal estimator in real time. For example, the patient health monitor applies statistical testing to determine the reliability of the real-time estimates of the stochastic variables by the optimal estimator. The statistical testing is performed in real time on residual errors of the optimal estimator to establish performance measures.

In one embodiment, the patient health monitor acts as an input/output interface between the patient or medical staff (e.g., a doctor, nurse, or other healthcare provider) and the optimal estimator. For example, environmental conditions can be provided to the patient health monitor for forwarding to the optimal estimator. Optimal estimator outputs can be provided to the patient health monitor for display or forwarding to an external device (e.g., a computer or a data storage device).

In one embodiment, the optimal estimator provides one or more outputs to an optimal controller which can regulate in real time the physiological parameter being monitored. For example, an optimal controller responds to real-time optimal estimator outputs and provides an output to operate an actuator. In the case of glucose control, the actuator can be a dispenser or a pump which secretes insulin to correct a relatively high glucose level and glucagon to correct a relatively low glucose level. The optimal controller takes advantage of a priori information regarding the statistical characteristics of the actuator and is able to control the output of the actuator to be within specified uncertainties.

In one embodiment, the optimal estimator and the optimal controller form an optimal closed-loop system. For example, a glucose sensor, an optimal estimator, an optimal controller, and an insulin/glucagon dispenser work together as an artificial pancreas to continuously regulate glucose level. The glucose sensor can be internal or external to a patient's body. The optimal controller provides a control feedback to the optimal estimator to account for delivery of the insulin/glucagon.

The optimal closed-loop system is effective in a variety of biomedical applications. For example, cardiovascular functions can be continuously regulated by using sensors to detect blood pressure, blood oxygen level, physical activity and the like, an optimal estimator to process the sensor measurements and make real-time estimates of heart function parameters, and an optimal controller to control operations of an artificial device (e.g., a pacemaker) in real time based on the real-time estimates from the optimal estimator to achieve a set of desired heart function parameter values. Other artificial devices (e.g., artificial limbs, bionic ears, and bionic eyes) can be part of similar optimal closed-loop systems with sensors detecting nerve signals or other appropriate signals.

The optimal closed-loop system is also effective in optimal treatment of chronic illnesses (e.g., HIV). Some medications for treatment of chronic illnesses are relatively toxic to the body. Over delivery of medication generally has adverse effects on the patient. The optimal closed-loop system is capable of providing effective and safe treatment for the patient. For example, an optimal estimator provides real-time estimates of key physiological parameters using one or more sensors, and an optimal controller controls a slow infusion of medication in real time based on the real-time estimates from the optimal estimator to obtain desirable values for the key physiological parameters.

In one embodiment, the optimal estimator, patient health monitor, and optimal controller are software algorithms which can be implemented using respective microprocessors. New information regarding process propagation or measurement relationship can be easily incorporated by modifying, reconfiguring, and/or adding to the software algorithms. The optimal estimator, patient health monitor, and optimal controller can be implemented as one joint algorithm or separate respective algorithms which function together to provide an optimal closed-loop system.

BRIEF DESCRIPTION OF THE DRAWINGS

FIG. 3B illustrates an initialization in one embodiment of an optimal estimator.

FIG. 3D illustrates a measurement-update cycle in accordance with one embodiment of an optimal estimator.

FIG. 6B illustrates one embodiment of a residual test data process in the patient health monitor.

FIG. 6C illustrates one embodiment of a statistical test process in the patient health monitor.

FIG. 9B illustrates one embodiment of a control model for a controller in accordance with the present invention.

FIG. 9C illustrates one embodiment of a control algorithm.

DETAILED DESCRIPTION OF THE INVENTION

The present invention involves application of real-time optimal estimation, optimized real-time decisions and displays (e.g., a patient health monitor), or optimal real-time control to physiological processes. In one embodiment, the real-time optimal estimation, the optimized real-time decisions and displays, and the optimal real-time control are implemented as separate modules which can be combined functionally. In an alternate embodiment, the real-time optimal estimation, the optimized real-time decisions and displays, and the optimal real-time control are implemented as one joint algorithm.

In one embodiment, input to an optimal estimator is provided by a physical sensor (or a plurality of sensors) which measures some arbitrary, but known, function (or functions) of variables or parameters to be estimated to within specified uncertainties and whose statistical characteristics are known. In one embodiment, an output of a real-time controller is provided to a physical controllable dispenser, or actuator, whose output is some known function of parameters to be controlled within specified uncertainties and whose statistical characteristics are known. In one embodiment, a decision and display function utilizes statistical testing of estimator residual errors using internally computed, and updated, estimator variances and covariances.

In one embodiment, the present invention is implemented as a software algorithm. The present invention uses models (e.g., dynamic process and measurement models). For best performance, the models should reflect the latest and most complete information available. As new and more complete information is developed, performance can be improved through incorporation of this information by simply modifying the software algorithm of the present invention.

Figure 1A:
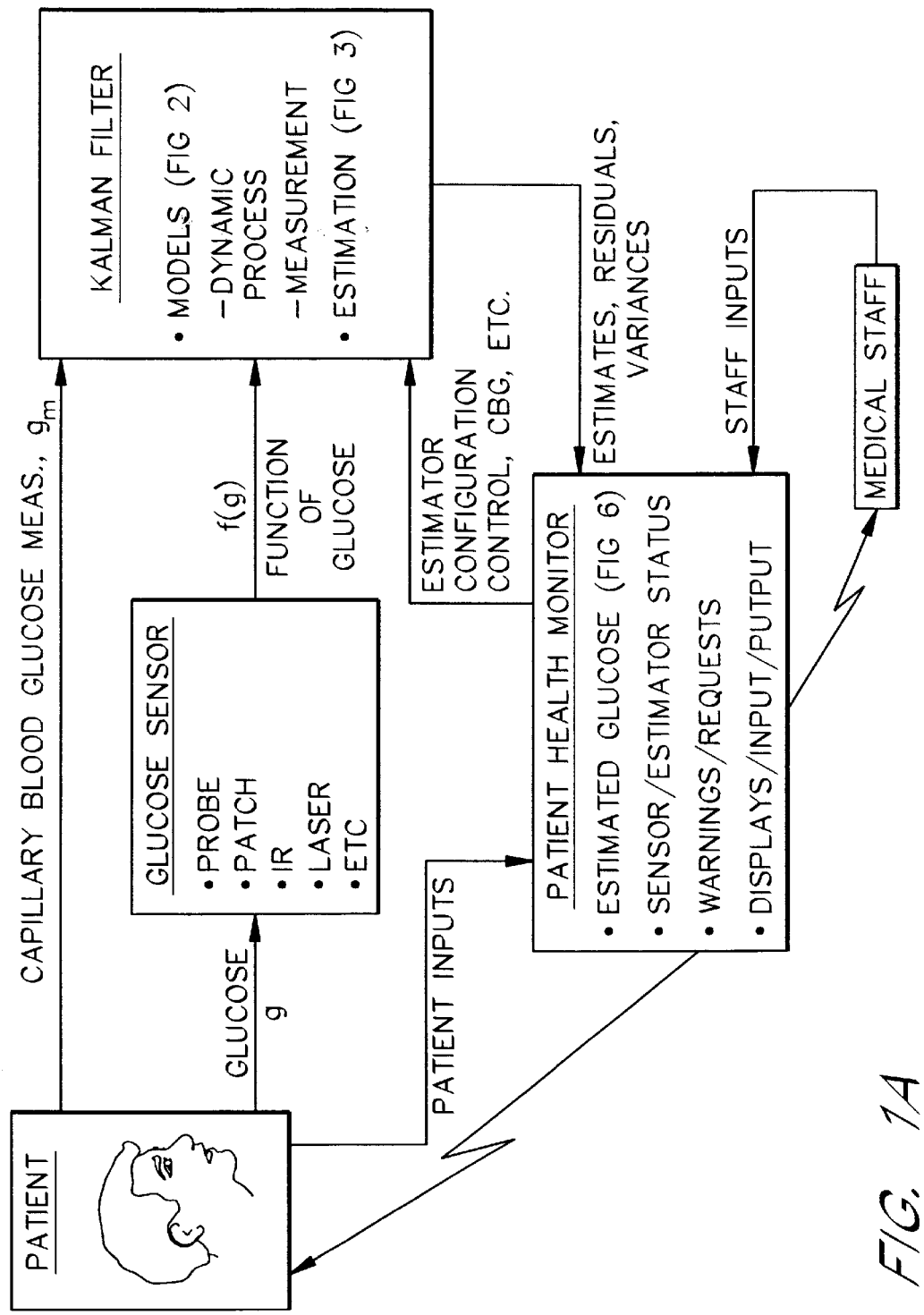
FIG. 1A is a block diagram of one embodiment of an estimator.

Embodiments of the present invention will be described hereinafter with reference to the drawings. FIG. 1A is a block diagram of one embodiment of an estimator. The estimator uses a linearized Kalman filter. The linearized Kalman filter accommodates nonlinear process models and/or nonlinear measurement models. In one embodiment, the linearized Kalman filter is a discrete extended Kalman filter which is linearized after each update using best estimates.

A general formulation of a continuous-discrete extended Kalman filter is provided in Table 1. In an alternate embodiment, the linearized Kalman filter is linearized about a nominal set for which a general formulation is given in Table 2.

The estimator computes an estimator gain based on time updated and measurement updated error variable variances and covariances. In one embodiment, the estimator is implemented using discrete formulations. In an alternate embodiment, the estimator is implemented using continuous formulations. In the actual development of algorithms, one can choose a Covariance formulation or an Information formulation depending on initialization uncertainty considerations. Further, the use of Bierman, factorization techniques (UDU^T) in the implementation leads to numerically stable algorithms which are excellent for operation over very long time periods.

In one embodiment, the estimator of FIG. 1A is applied to the problem of monitoring patient glucose levels. Any type of physical sensor which measures some function of glucose can be used. In one embodiment, one or more capillary blood glucose (CBG) measurements are obtained on initialization of the estimator and when estimated glucose deviations exceed computed variance levels.

In another embodiment, additional capillary glucose values are obtained on a periodic basis to assess sensor function. As an example, CBG measurements may be obtained once or twice a day pre and one hour post prandial or when the estimator determines that the glucose values are out of range of predetermined limits.

In one embodiment, the estimator is contained in a small portable package. The estimator can be operated by a patient. Alternatively, the estimator can be operated by medical staff in a hospital or clinic. The estimator (e.g., Kalman estimator) uses a Kalman filter to provided real-time estimates of patient glucose levels based upon glucose sensor measurements. The Kalman estimator can also use additional information to more closely predict time propagation of glucose levels, such as exercise, food intake, insulin administration, or other factors which influence glucose levels or the function of the sensor (e.g., local pH, temperature or oxygen tension near the physical sensor).

Figure 1B:
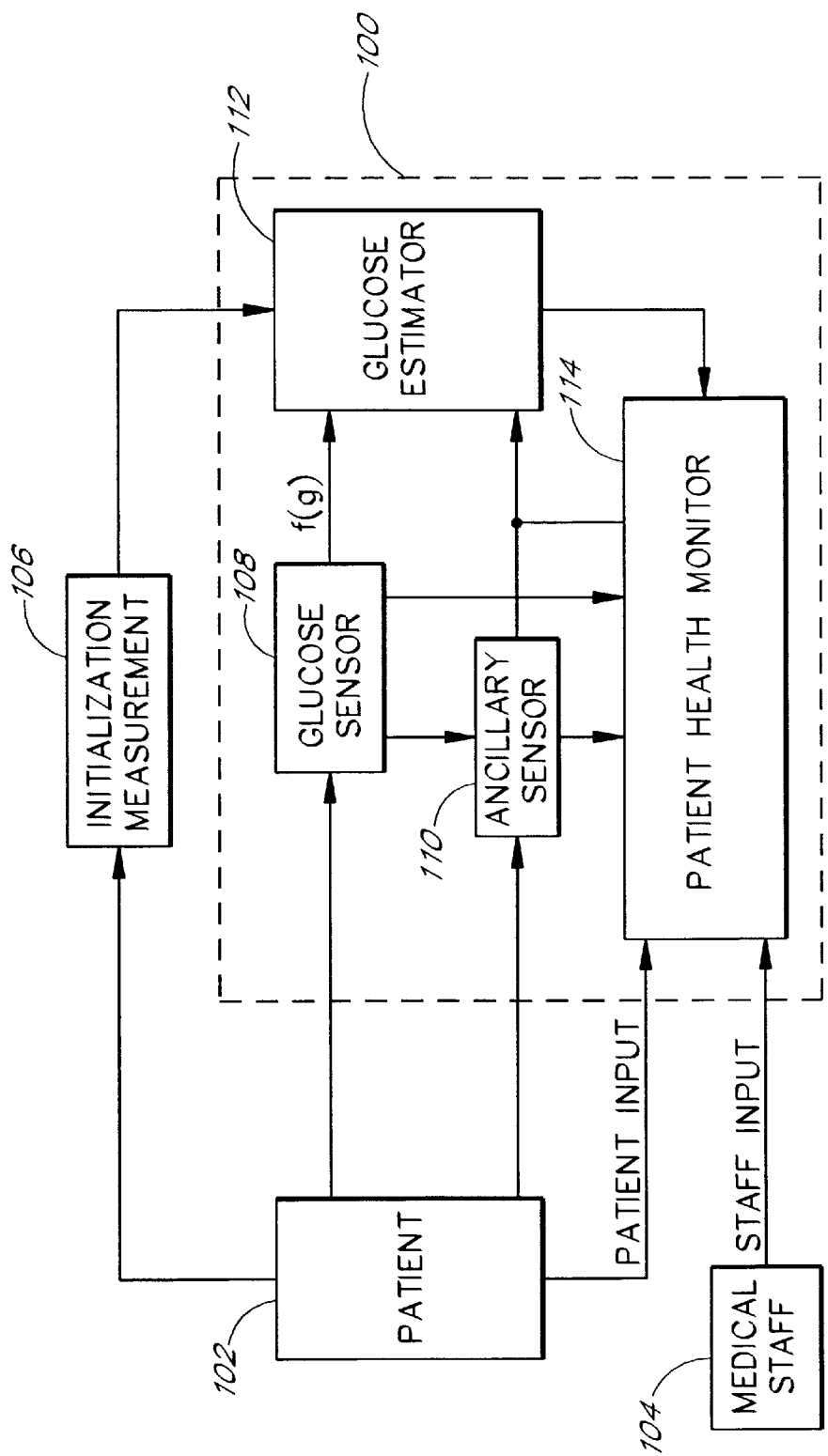
FIG. 1B is a block diagram of another embodiment of a glucose-monitoring device.

FIG. 1B is a block diagram of one embodiment of a glucose-monitoring device 100. The glucose-monitoring device 100 includes a glucose sensor 108, an ancillary sensor 110, a glucose estimator 114, and a patient health monitor 114. The glucose-monitoring device 100 is used to provide real-time glucose estimates of a patient 102. In one embodiment, the glucose-monitoring device 100 is an integrated unit which is portable by the patient 102 to provide continuous glucose monitoring and real-time displays. The glucose sensor 108 (e.g., a probe, patch, infrared, or laser sensor) is coupled to the patient 102 and outputs a measurement f(g) which is a function of the glucose level of the patient 102. The glucose sensor 108 makes measurements within specified uncertainties and has known statistical characteristics. The glucose sensor 108 provides the measurement f(g) to the glucose estimator 112. In one embodiment, the glucose sensor 108 makes measurements periodically. In an alternate embodiment, the glucose sensor 108 makes measurements intermittently or upon command.

The ancillary sensor 110 is coupled to the patient 102, the glucose sensor 108, and/or surroundings of the patient 102 and/or glucose sensor 108 to provide information regarding environmental and/or glucose sensor conditions (e.g., temperature, humidity, local pH, etc.) which affect the measurement. One or more outputs of the ancillary sensor 110 are provided to the glucose estimator 112. In one embodiment, the ancillary sensor 110 provides outputs to the patient health monitor 114 which can process the information for display or for forwarding to the glucose estimator 112. In an alternate embodiment, the ancillary sensor 110 is not a part of the glucose-monitoring device 100.

The patient 102 and/or a medical staff 104 (i.e., a user) can provide information on the environmental and glucose sensor conditions as well as other information affecting the measurement. In one embodiment, the patient, 102 and/or medical staff 104 inputs information (e.g., exercise activity, food intake, insulin administration, etc.) using the patient health monitor 114. The patient health monitor 114 acts as an input/output interface or a means for the user to configure the glucose estimator 112. The patient health monitor 114 forwards the information to the glucose estimator 112.

In one embodiment, the patient health monitor 114 is a display device. For example, an output of the glucose estimator 112 (e.g., an optimal real-time estimate of glucose) is provided to the patient health monitor 114 which displays the information in a comprehensible format for the patient 102 and/or the medical staff 104. The patient health monitor 114 can also contemporaneously display information provided by the glucose sensor 108, the ancillary sensor 110, the patient 102 and/or the medical staff 104 which affects the measurement used to make the optimal glucose estimate.

In another embodiment, the patient health monitor 114 is a status indicator. For example, the glucose estimator 112 provides outputs (e.g., residuals and variances) to the patient health monitor 114 which applies statistical testing to determine the reliability of the glucose sensor 108 and/or the glucose estimator 112. The patient health monitor 114 provides a warning when poor performance is detected.

In one embodiment, the glucose estimator 112 is a linearized Kalman filter (e.g., a discrete extended Kalman filter) to account for a nonlinear process model and/or measurement model. The glucose estimator (or Kalman estimator) 112 provides real-time estimates of the glucose level in the patient 102. An initialization measurement 106 (e.g., a CBG measurement) is obtained from the patient 102 and provided to the Kalman estimator 112 to initialize the Kalman estimator 112.

Figure 2:
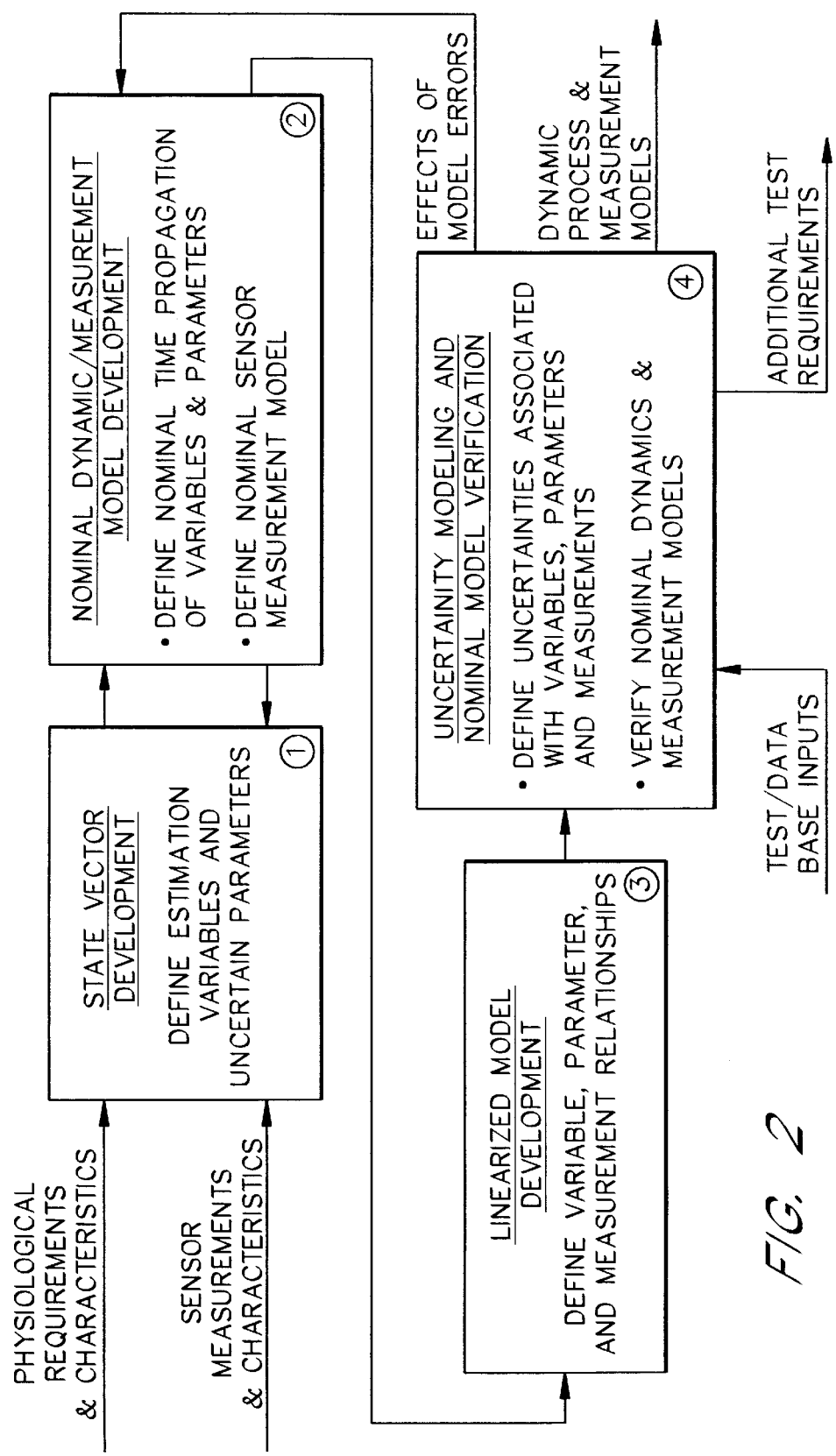
FIG. 2 illustrates one embodiment of modeling physiological processes in a linearized Kalman filter application.

FIG. 2 is a flow chart illustrating one embodiment of a modeling process for physiological processes. In one embodiment, physiological processes are described by nonlinear stochastic models. In one embodiment, the flow chart of FIG. 2 illustrates one method of developing a dynamic model for an optimal estimator. The method includes steps for state vector development, nominal dynamic/ measurement model development, linearized model development, and uncertainty modeling and nominal model verification.

FIG. 2 illustrates modeling of physiological processes in a linearized Kalman filter application. As an example in glucose estimation, in a first block of FIG. 2, glucose is an estimation variable. The time rate of change of glucose might become another estimation variable. An uncertain parameter might be the glucose sensor scale factor, and additionally, the rate of change of scale factor over time could be another.

In one embodiment of a second block of FIG. 2, the way in which variables and parameters nominally propagate over time may change with conditions. In the example of glucose estimation, inputs can be used to identify patient related activities: eating; exercising; sleeping; insulin injection; etc. With these identified patient related activities, additional state variables can be identified and modeled. For example, if patient eating can be related to a change in glucose level over some specified time interval, dynamics can be implemented within the estimator model which will propagate (or extrapolate) a rise in the glucose level over that time interval. This rise may be modeled by appropriate functions whose variables contain uncertainties, which may be added as elements of the state vector. In an analogous way, decreases in glucose levels (e.g., due to insulin injections) can be modeled. These models may be general in nature, or they may be patient specific. Consequently, patient related activities that have a significant impact on glucose levels, or the rate of change of glucose levels, can be accounted for within the dynamic process model.

Insofar as sensor modeling is concerned, experience shows that, for example, infrared sensor measurement bias errors vary with, among other things, temperature. If this variation with temperature can be modeled, and included in the process model, then a temperature measurement will improve estimator performance. A particular physical glucose sensor may have a scale factor which has a characteristic decay in sensitivity over time as discussed in further detail below. There may be other variables that can be measured which will affect the physical functions of a sensor such as local pH, oxygen tension, etc.

In one embodiment, the nominal modeling is comprised of three types: 1) predictable characteristics of a physical sensor function over time (e.g., a fixed rate in decline of sensor output), 2) other measurable physical variables which may affect sensor function (e.g., local temperature, pH, etc.), and 3) predictable changes in the model which occur with patient related activities (e.g., exercise, eating or insulin administration). Changes to the dynamic process model may add variables and/or uncertain parameters to the state vector and changes to measurement models. As a result, the activities indicated in blocks 1 and 2 of FIG. 2 constitute an iterative process.

In one embodiment of block 3 of FIG. 2, the relationship between variables, parameters, and measurements determines which parts of the processes and measurements are nonlinear and are linearized. Further, the relationship between variables, parameters, and measurements determines if the variables and parameters are observable and can be estimated. In certain cases, observability can be enhanced through introduction of additional modeling information. For the glucose example, the ability to estimate sensor scale factor and/or detect sensor failure may be improved by modeling glucose propagation changes due to insulin injections or ingestion of sugar. For example, tracking known changes enhances scale factor observability through estimator generated correlations. Further, if it is known that glucose levels vary and the sensor measurement does not change accordingly within prescribed levels of uncertainty, a sensor problem is indicated.

In one embodiment of block 4 of FIG. 2, the development of a relatively large database is used to empirically verify and/or modify the nominal nonlinear dynamic process/measurement models and derive uncertainty levels associated with the variables, parameters, and measurements. In one embodiment, the empirical data can be fitted to nonlinear functions using a nonlinear regression package contained in a commercially available software application program such as "Mathematica" from Wolfram Research, Inc. Analytical functions may be added or modified using the test database. The repeatability of the fit over nominal ranges of the patient environment determines the uncertain parameters and the variations establish uncertainty levels. The more accurate the dynamic process and measurement models, the more the uncertainties are reduced, and the greater the estimator performance. As the process evolves, the modeling becomes better defined through iterations between blocks 4 and 2. Certain portions of the models may be developed on an individual basis (e.g., for a specific patient).

A database is used to empirically develop and verify models. An embodiment discussed below uses the database to develop two separate dynamic process models. For example, after processing a number of data sets from a physical sensor that was used to monitor the glucose level of various patients, it was observed that the sensor scale factor was equally likely to move up or down over the first fifteen to twenty-five hours. However, the scale factor tended to decay for the remaining life of the sensor after this period of time, usually three or four days. These observations are incorporated in an embodiment of the estimator discussed in further detail below.

Figure 3A:
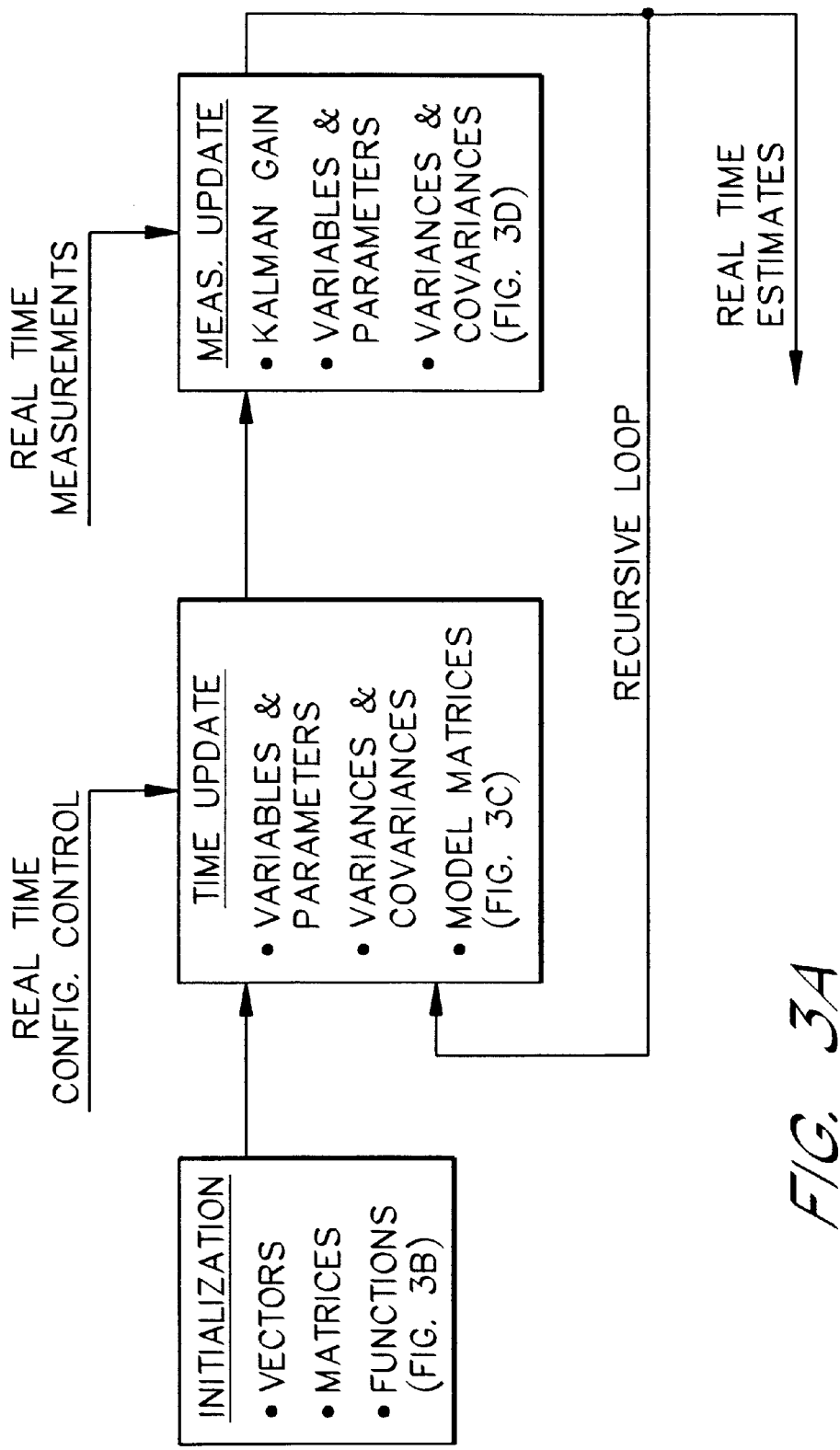
FIG. 3A describes one embodiment of an estimation function which depicts a linearized Kalman filter formulation.

FIG. 3A describes an estimation function which depicts a linearized Kalman filter formulation. In one embodiment, the particular form is that of a discrete extended Kalman filter which linearizes after each update using best estimates. In the formulation, a vector whose elements comprise variables and/or parameters (with uncertainties) for making estimates defines the state of a system.

There is a distinction between variables (e.g., random variables) and parameters with uncertainty. Variables, such as glucose and rate of change of glucose, are estimated and can be controlled (if control is implemented). Parameters with uncertainty are part of the model structure not known precisely and are estimated and updated (like variables) but not controlled, e.g., a glucose sensor scale factor or insulin dispensing controller scale factor.

In one embodiment, real-time variable and parameter estimates are used to re-linearize the model following each update. Inputs to the estimator can consist of any measurement which is related to, or can be correlated with, any element in the state vector. In the case of glucose estimation, other inputs can consist of dynamic process configuration control based on patient related activities or other circumstances. Following initialization, the time update and measurement update cycles form a recursive loop. The time update period is the time interval between the receipt of measurements. This is a function of the sensor and of acceptable latency in the estimates.

Figure 3C:
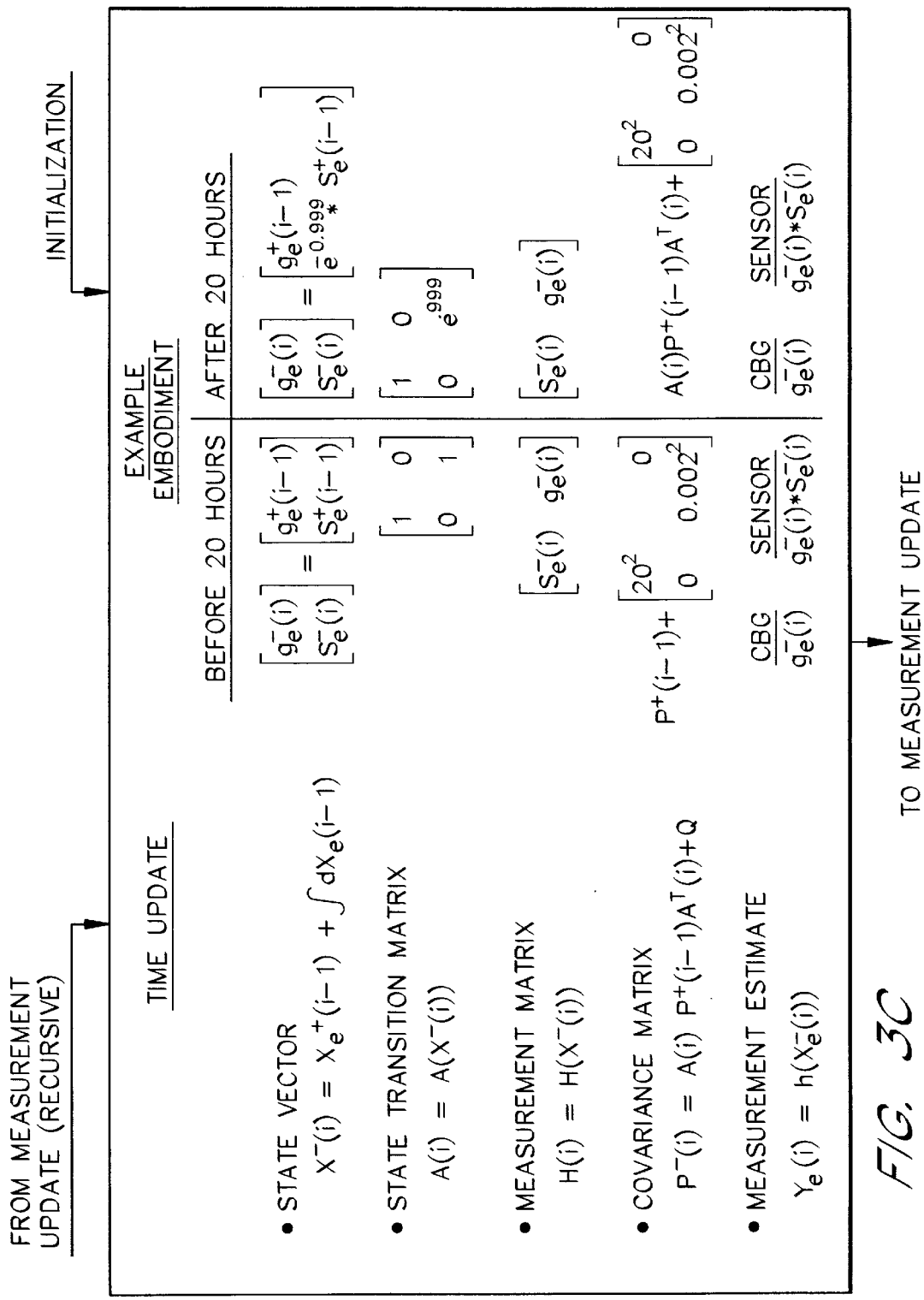
FIG. 3C illustrates a time-update cycle in accordance with one embodiment of an optimal estimator.

FIGS. 3B, 3C and 3D illustrate, respectively, Initialization and the recursive Time Update and Measurement Update cycles according to one embodiment of the present invention. Table 3 defines, in more detail, symbols used in these figures. In one embodiment, dynamic process and measurement modeling is contained in software algorithms with parameter and structure updates in real time.

One embodiment of an initialization of the estimation process is described in FIG. 3B. A state vector estimate, Xeo, contains the initial estimates of the process variables and model parameters with uncertainty, while the covariance matrix, Po, contains the initial variances and covariances associated with the Xeo elements.

FIG. 3B shows an example embodiment with a two-element state vector which is based on empirical observations described above. As an example, the point in time when the scale factor begins to decay was chosen as 20 hours, a nominal value over the database. An exponential decay was chosen to model this decay rate and is consistent with the first derivative of scale factor equal to a parameter, alpha, multiplied by the variable scale factor. In this case, alpha is not modeled as an uncertain parameter; a value of 0.012 was chosen as a nominal value, over the database, for the five-minute cycle time of this physical sensor.

The initial estimate of glucose is 150 mg/dl (state vector element) with an initial uncertainty variance of 100 mg/dl squared (a covariance matrix element). When processing the data, the glucose element was initialized by setting it substantially equal to the first capillary blood glucose measurement. The nominal initial scale factor value, for the physical sensor, is 0.25 nano-amps/(mg/dl) with a parameter uncertainty (variance) of 0.1 nano-amps/(mg/dl) squared.

The initial covariance between the glucose variable and the scale factor parameter is zero. Correlation between glucose and scale factor will develop as the estimator processes the sensor measurements. Each type of sensor will have its own model and characteristics. The measurement uncertainty is 5 nano-amps squared, an element of the R matrix. In one embodiment, this is a scalar measurement and the R matrix contains a single element.

A second measurement in this example embodiment is an occasional direct measurement, such as a capillary blood glucose measurement (CBG), with a unity scale factor, and a measurement error uncertainty of 15 mg/dl squared (a single element in a second R matrix). This is probably better modeled as 15% of the measured glucose value. The growth in uncertainty of glucose and scale factor from measurement to measurement is, respectively, 20 mg/dl squared and 0.002 nano-amps squared (elements of the process noise matrix, Q).

FIG. 3C illustrates a time-update process of the recursive process in one embodiment of an optimal estimator. In this figure, a negative superscript indicates a time update while a positive superscript indicates a measurement update. In the brackets, a letter "i" indicates time at the ith interval and (i−1) indicates time at the previous time interval. In an update process, a state vector is first updated since these elements are used to update matrices and to bring the time epoch of the estimated measurement to be consistent with that of the next measurement to be received.

In an example embodiment with a two-element state vector, the dynamic process is linear. With no patient inputs, the first derivative of the measured physiologic variable is zero, corresponding to the case when the level (on average) is as likely to either go up or to go down. No additional a priori information is assumed about the time propagation of glucose.

In one embodiment of estimating glucose, the solution to the scale factor propagation after the first 20 hours is defined by the exponential shown in the second column. Consequently, for this embodiment, the dynamic process function (f), is linear, is not a function of state vector elements, and, from linear system theory, the transition matrix (A) is the 2 by 2 identity matrix for the first 20 hours and thereafter is defined by the 2 by 2 matrix in the second column.

In one embodiment, the measurement function (h) for the sensor measurement is non-linear in the state vector elements. If Ge and Se are used to denote glucose and scale factor estimates, respectively, then Ye=Se*Ge. Definitions of the above terms are provided in Table 3. When linearized using best estimates, the linearized measurement matrix H=[Se Ge] and is of the same functional form both before and after 20 hours.

FIG. 3D illustrates a measurement-update process of one embodiment of an optimal estimator. The measurement update sequence begins with the computation of the gain matrix, K(i). The difference between the actual sensor measurement and the best estimate of the measurement is computed: y(i)=Ym(i)−Se(i)*Ge(i). This difference, or residual, when multiplied by the gain matrix and added to the time-updated estimate produces the measurement-updated estimate.

The covariance matrix is then measurement updated, reflecting the level of uncertainty in the estimates following the processing of a measurement. In the glucose example, if a second measurement is available, such as a CBG, then the measurement sequence is again cycled through, starting with a new gain computation, and using the appropriate measurement matrix and new best estimate of the next measurement. Following the processing of all available measurements at the ith time epoch, the updated state vector and covariance matrix are then used to start the time update for the (i+1)th time epoch which begins the next cycle.

One embodiment of an estimation algorithm illustrating the initialization, the time update process, and the measurement update process discussed above is provided in Table 4. Table 4 is an algorithm programmed in the MATLAB language (from Math Works). This printout defines a working program and has been used to process a significant number of data sets. In the glucose example, the estimation results from the process of two data files, both gathered from the same patient, and taken about a month apart, are shown in FIGS. 4A, 4B, 5A, and 5B.

In one embodiment, sensor inputs are provided and processed every 5 minutes. Occasional CBGs are also provided. For example, two CBGs per day were processed by an estimator; and additional CBG values were used to judge estimator performance by comparing glucose estimates with actual CBG values not used by the estimator.

Figure 4A:
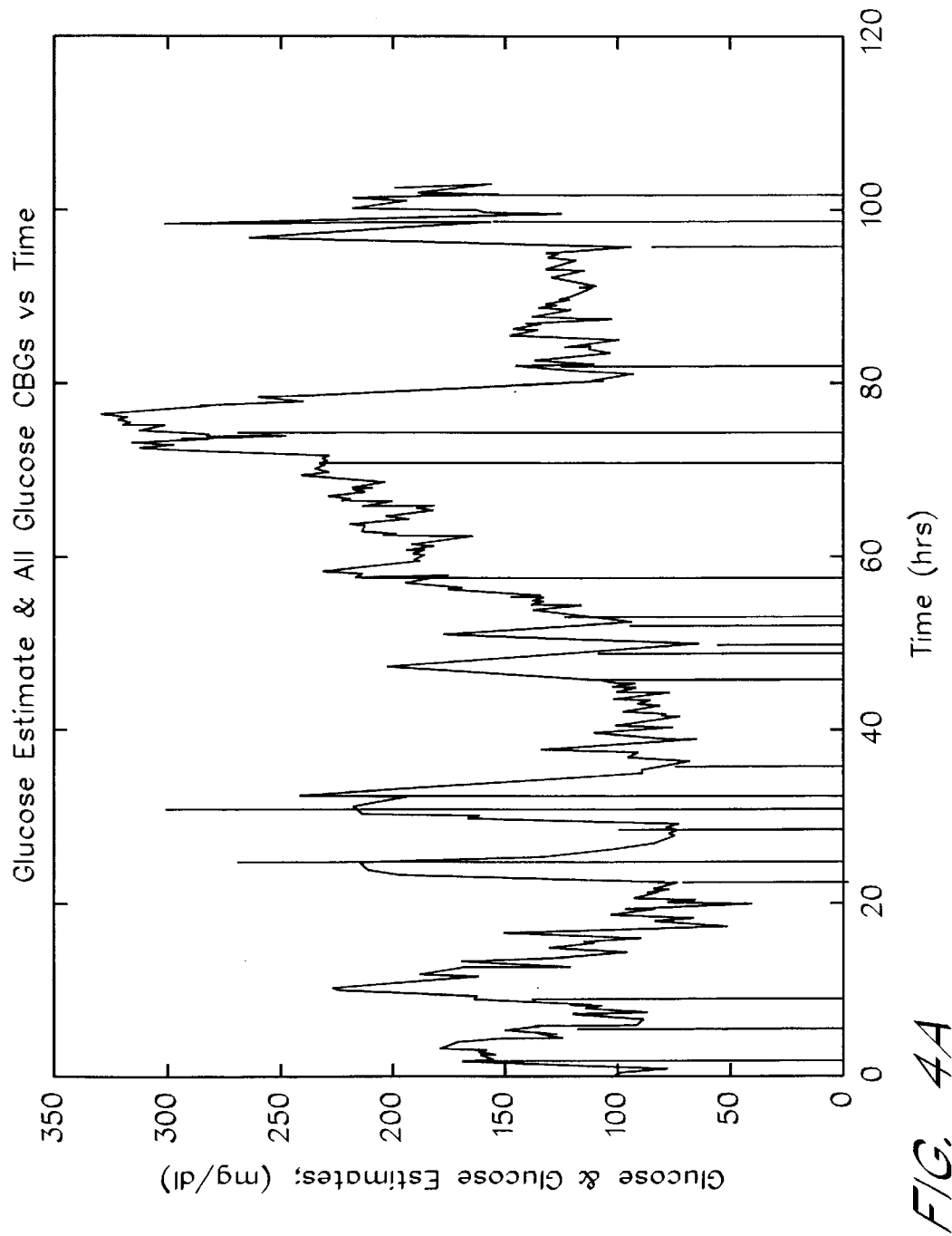
FIGS. 4A and 4B illustrate a first set of time history plots of optimal glucose estimates and CBG measurements with respect to time.
Figure 4B:
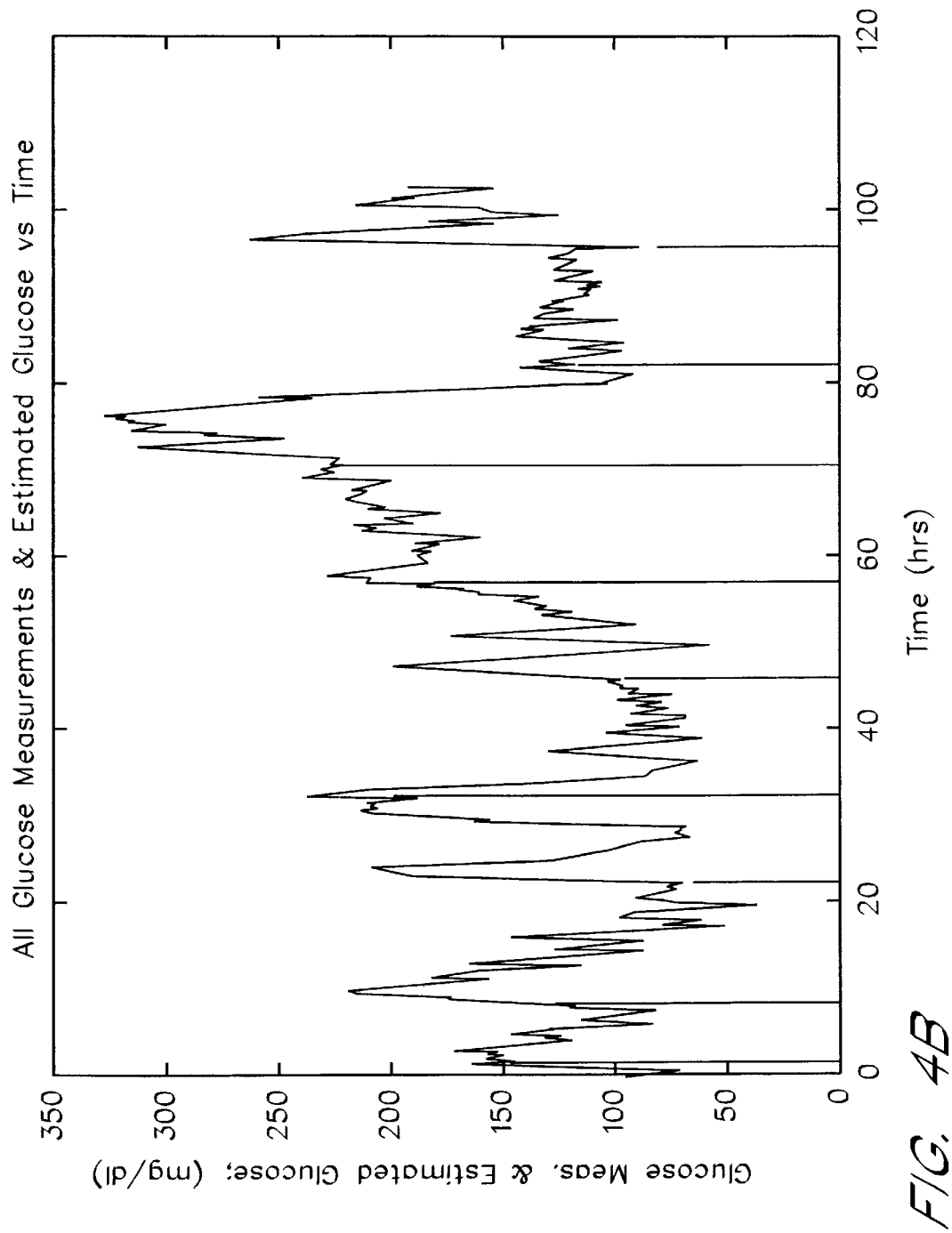

FIGS. 4A and 4B illustrate a first set of time history plots of optimal glucose estimates and CBG measurements with respect to time. FIG. 4A shows a time history of the real-time estimates of glucose (e.g., every 5 minutes) along with all available discrete CBGs.

FIG. 4B shows a time history of the glucose estimates along with CBGs that were processed. In this figure, the estimated glucose value took several rapid swings between approximately 48 hours and 58 hours. FIG. 4B indicates that only sensor measurements were processed during that interval and no CBGs were processed. However, the CBGs plotted in FIG. 4A indicate that the glucose estimates did tend to follow the excursions of the patient glucose levels.

Figure 5A:
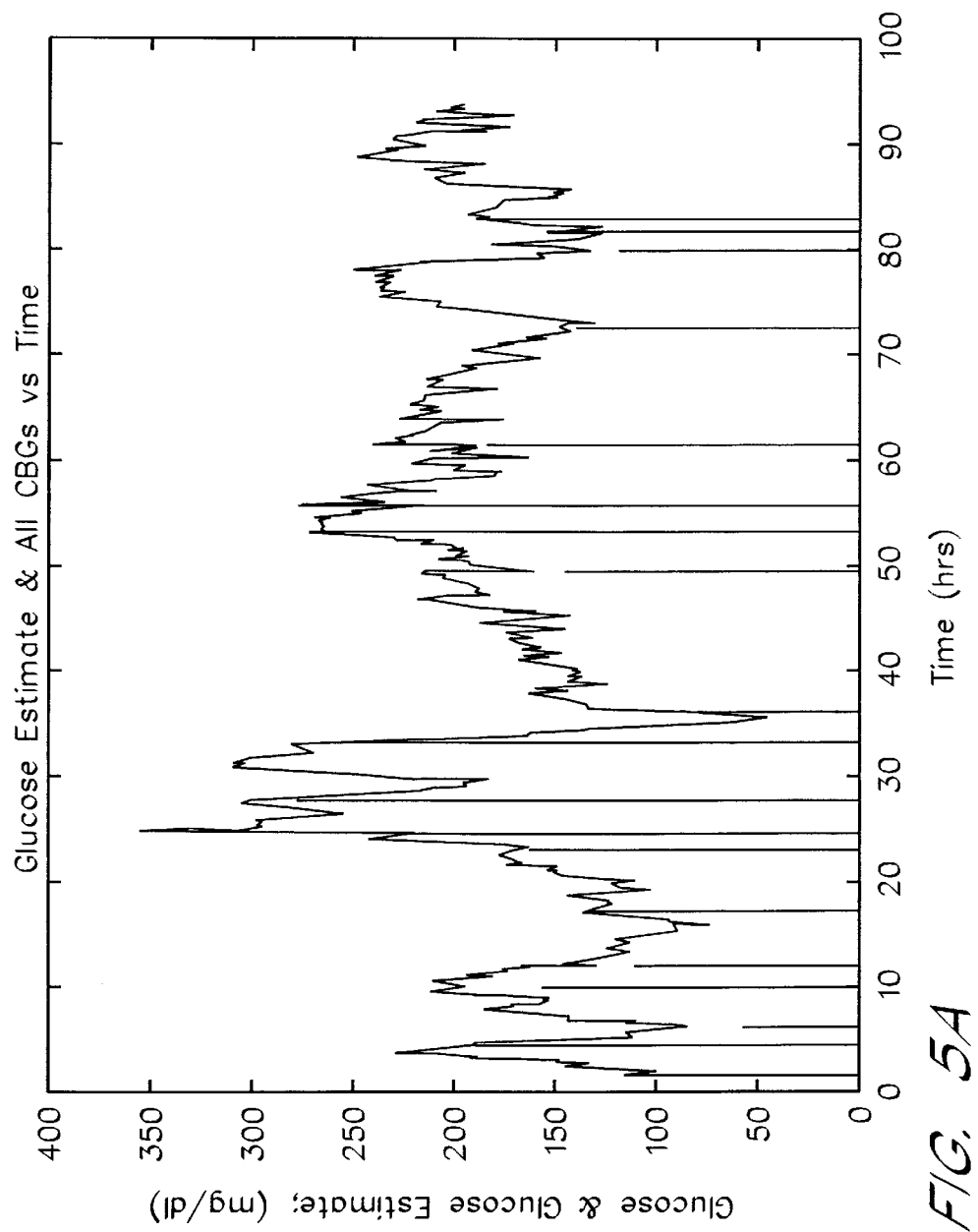
FIGS. 5A and 5B illustrate a second set of time history plots of optimal glucose estimates and CBG measurements with respect to time.
Figure 5B:
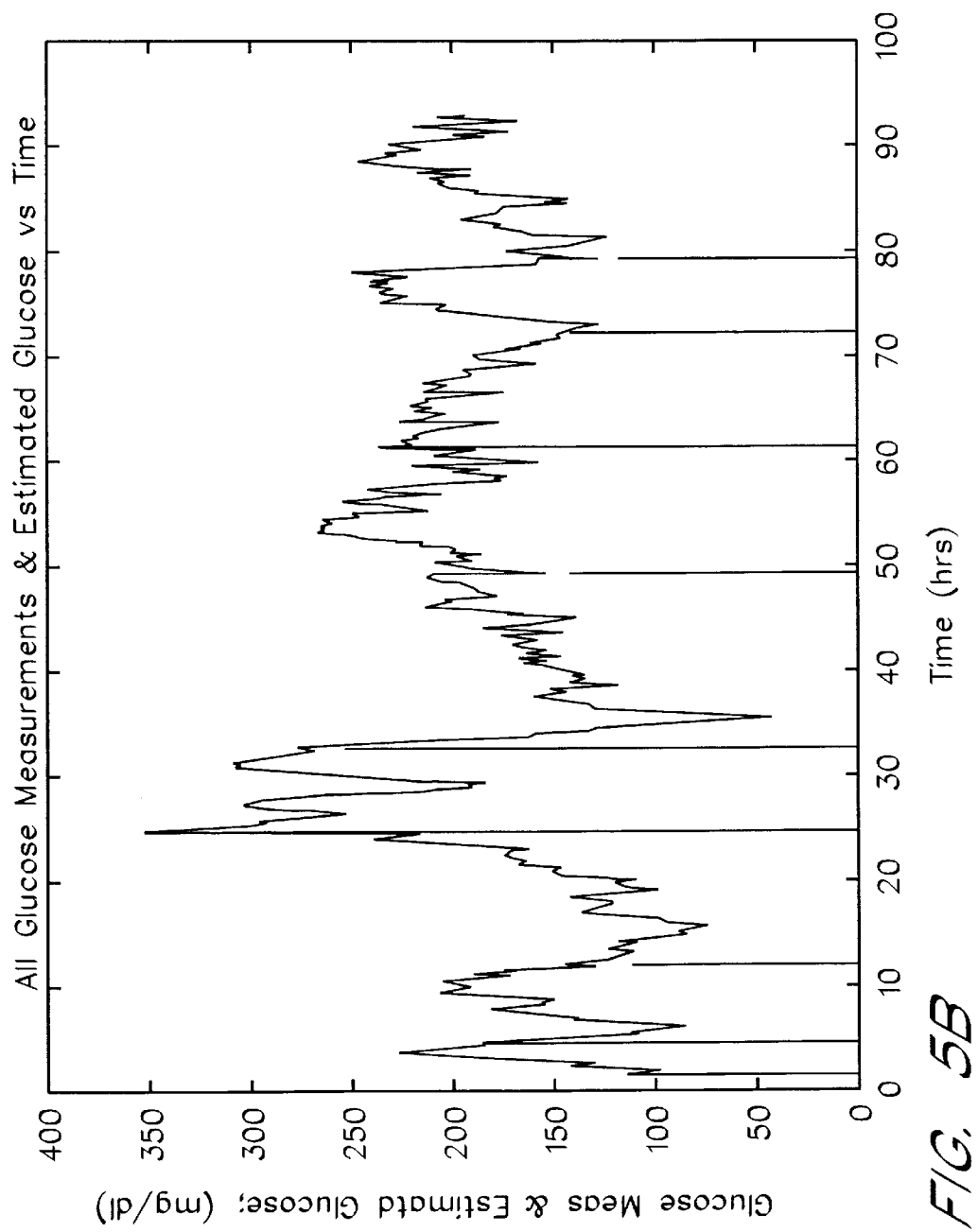

FIGS. 5A and 5B illustrate a second set of time history plots of optimal glucose estimates and CBG measurements with respect to time. The time duration for these runs is about 4 days without patient inputs. Over this time period, the patient ate, slept, exercised, and took insulin injections. Dynamic models to account for these activities, much like the decaying scale factor, could be implemented and called into use upon command.

Figure 6A:
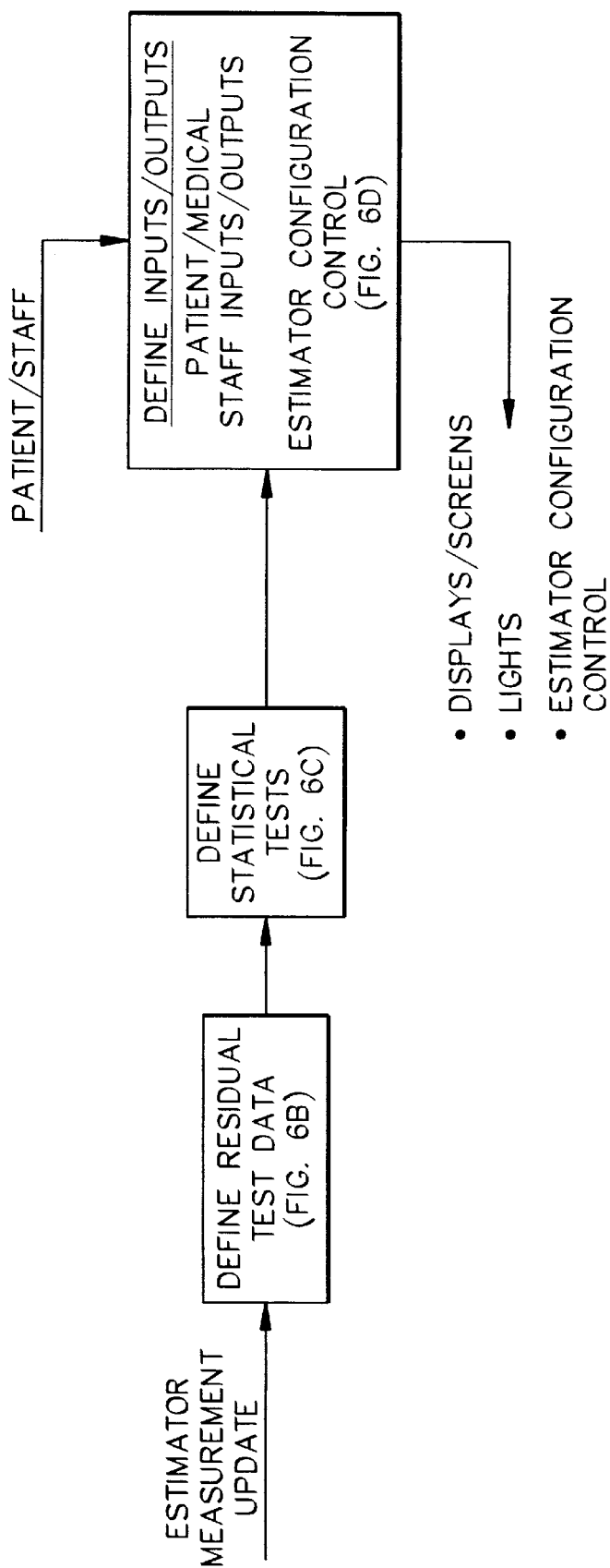
FIG. 6A is a block diagram of one embodiment of a patient health monitor.

FIG. 6A is a block diagram of one embodiment of a patient health monitor. On example of an algorithm for the patient health monitor is in Table 4 which generates statistical test data based on Kalman filter residuals as well as test displays. In one embodiment, the patient health monitor generates real-time decisions and displays which are integrated with a Kalman filter. The patient health monitor allows the patient or medical staff to interact with a Kalman estimator and/or Kalman controller described herein.

In one embodiment, the patient health monitor provides insight into how well a Kalman filter is working through the filter residual that is the difference between the estimate of the measurement at the time the measurement is received and the actual measurement. In another embodiment, other checks are used from time to time, such as the CBGs in the glucose example described above. An example of another check on the status of a sensor is through the use of patient inputs or signals indicating that something is changing in a prescribed way and then noting whether or not the sensor is observing this change within prescribed uncertainties.

In one embodiment, the real-time displays and decisions of the patient health monitor uses some occasional outside checks but relies substantially on results of statistical testing performed on filter residuals. If estimates of the measurements are, on average, good (e.g., residuals are small and unbiased), then the estimator is generally working well, and vice versa. More specifically, elements of the covariance matrix can be used to construct statistical test applications.

For hospital applications, real-time displays of glucose estimates along with real-time displays of estimator performance test results can be important visual inputs to the medical staff. Requests for additional CBG measurements or the sounding of an alarm in the event glucose estimates exceed critical limits may also prove useful. In one embodiment, a reduced number of outputs is provided in relatively small estimators for individual use.

FIG. 6B illustrates one embodiment of a residual test data process in the patient health monitor. For example, the residual (y), covariance matrix (P), measurement matrix (H), and measurement noise matrix (R) are available from an estimator algorithm at each time epoch (i). If the estimator is operating properly, the sequence of residuals has the property of zero mean, white noise sequence, i.e., any two residuals taken at different times are uncorrelated ($E[y(i)*y(j)]=0$, for all j not equal to, i). This condition provides a unique means for constructing statistical tests.

Visually, a time history plot of the residuals, Sy(i) in FIG. 6B, should appear random, zero mean, and unbaised. If they are summed over time, the deviation of the sum from zero should, on average, grow as the square root of time, as should its absolute value, ASy(i). The fact that $E[y(i)*y(j)]=0$, for i not equal to j, also means that the sum of the variances, SV(i) in FIG. 6B, which is easily computed, is equal to the variance of the sum of residuals for a properly performing estimator. The standard deviation of the sum of residuals, StdSV(i) also grows as the square root of time.

FIG. 6C illustrates one embodiment of a statistical test process in the patient health monitor. FIG. 6C defines statistical tests which can be constructed based on filter residual test data. One of these compares the absolute value of the sum of the residuals with the standard deviation of the sum of residuals. On average, the ASy(i) should be bounded by the StdSV(i). If not, this indicates that the deviations of Sy(i) are growing faster than that of a white noise sequence, implying degraded estimator performance.

Figure 7A:
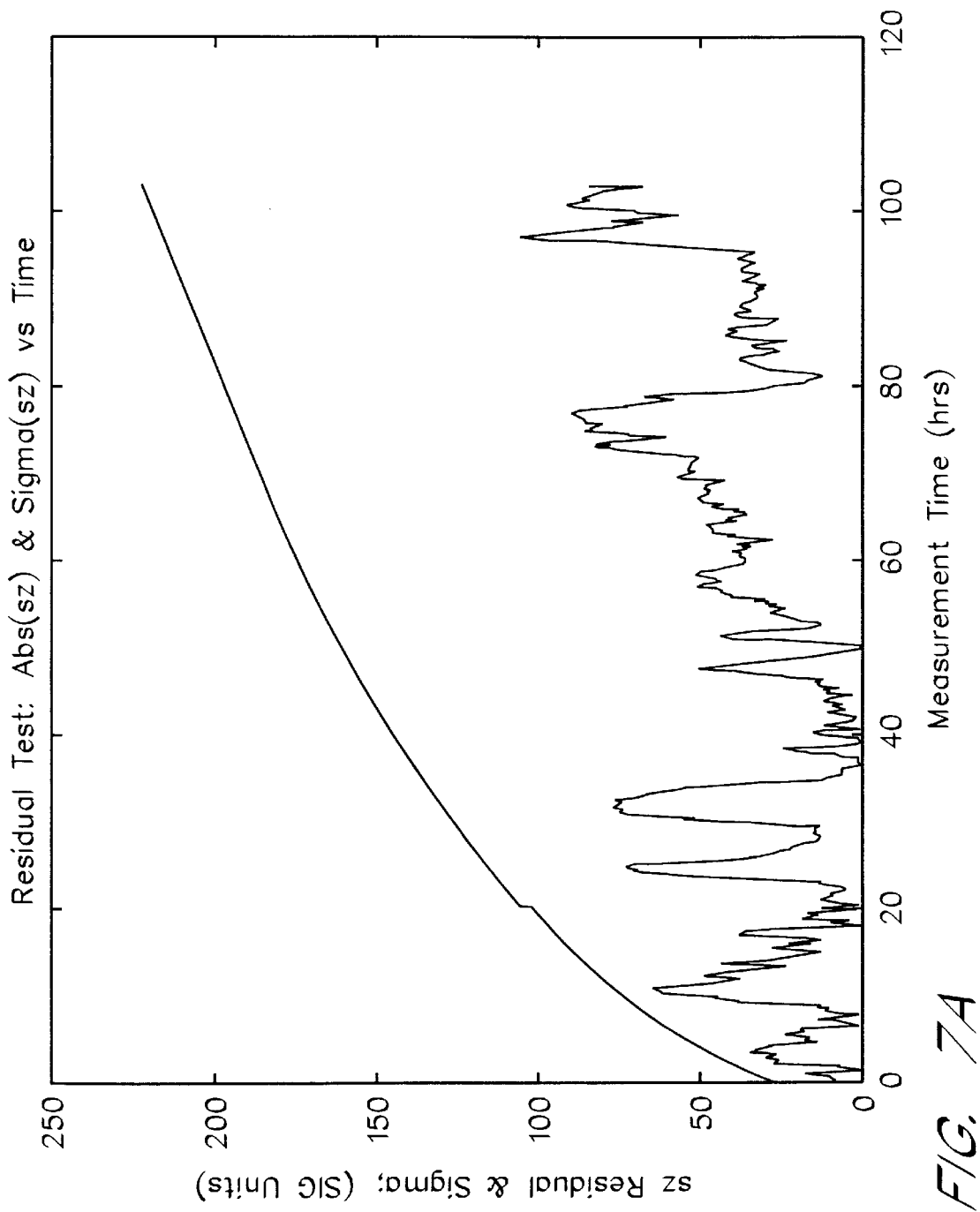
FIGS. 7A and 7B illustrate time history plots of residual test data with respect to measurement time.
Figure 7B:
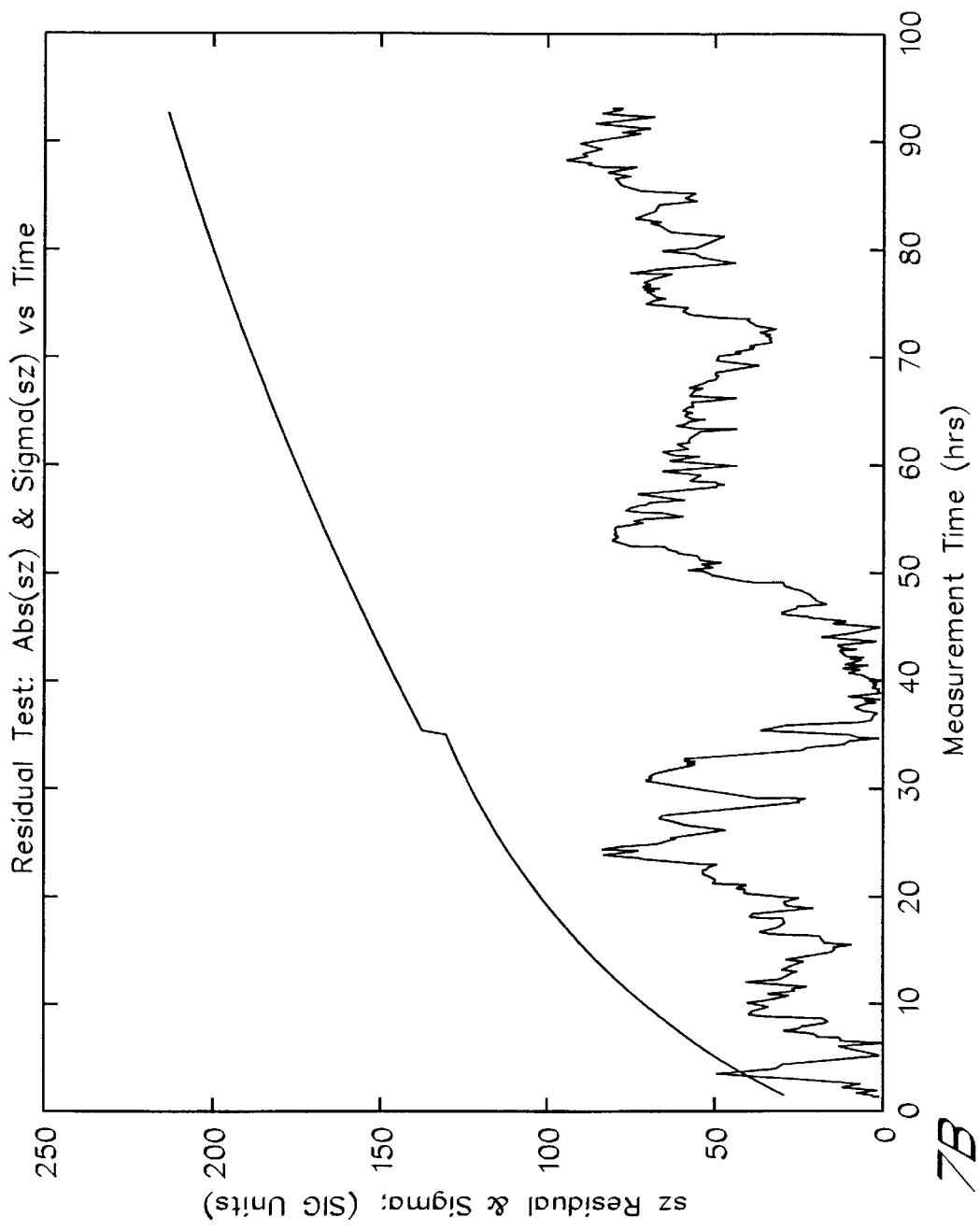

Real-time displays of ASy(i) and StdSV(i) histories can provide a visual picture of estimator performance. An example is provided in FIGS. 7A and 7B which illustrate time history plots of residual test data with respect to measurement time. These two plots are one form of residual tests for the two sets of glucose estimation results provided in FIGS. 4A, 4B, 5A, and 5B respectively. In both cases, the sum of residuals are well behaved and was bounded by the Standard Deviation, Std, of the sum of residuals.

The example embodiment for the glucose application of test data, test generation, and test result display described above is implemented by the algorithm in Table 4. Other real-time quantitative tests can also be constructed using these data. Tests on individual residuals can be performed using individual variances. If a measurement is received which causes the residual to exceed a four signal level, for example, the action might be to emit a warning and request an immediate CBG measurement. Other tests are identified in FIG. 6C and will be evaluated as the system develops.

Figure 6D:
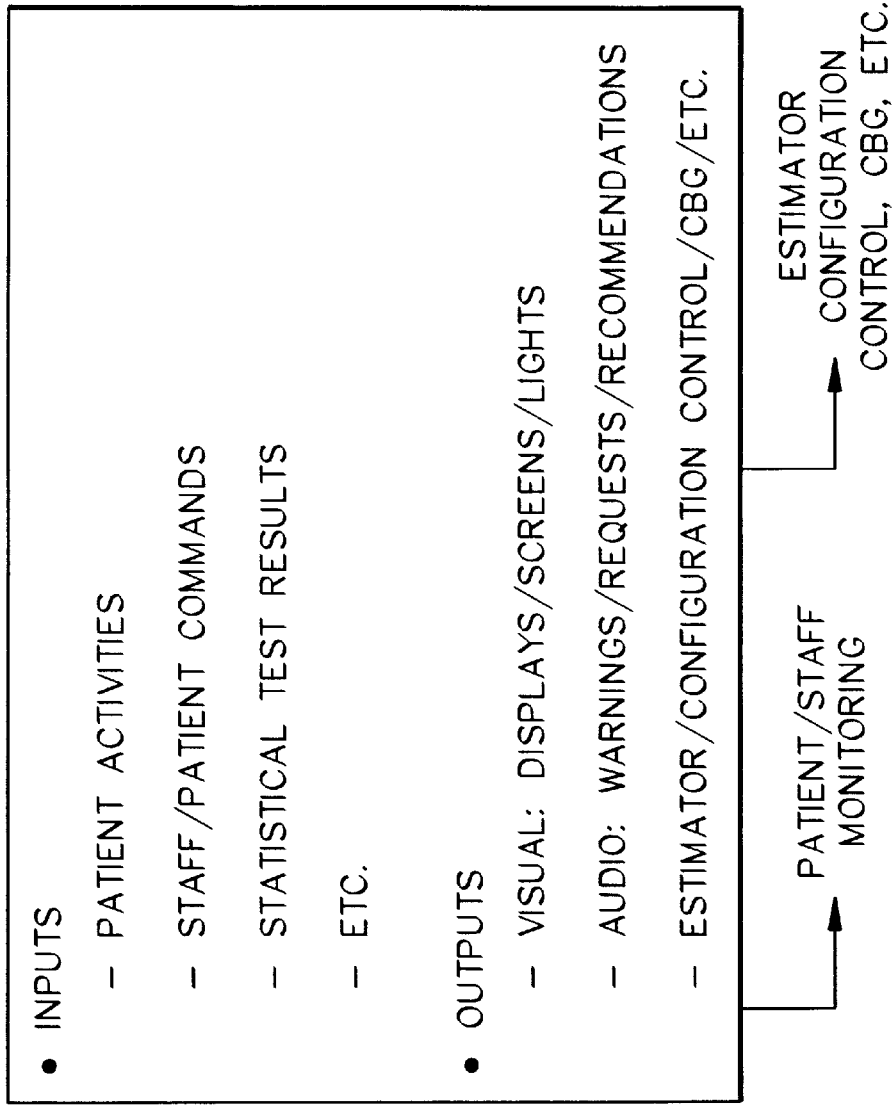
FIG. 6D illustrates one embodiment of an input/output interface in the patient health monitor.

FIG. 6D illustrates one embodiment of an input/output interface in the patient health monitor. The patient health monitor provides a capability for the patient and/or staff to communicate and interact in real time with estimation and control processes using simple commands, visual displays, and audio outputs described above. Confidence levels in estimator performance can be established and a genuine interface established whereby the estimation and control processes could request additional information to check and insure confidence in estimates, physical sensors, and physical controllers. The staff can provide useful real-time inputs to augment this process.

Figure 8:
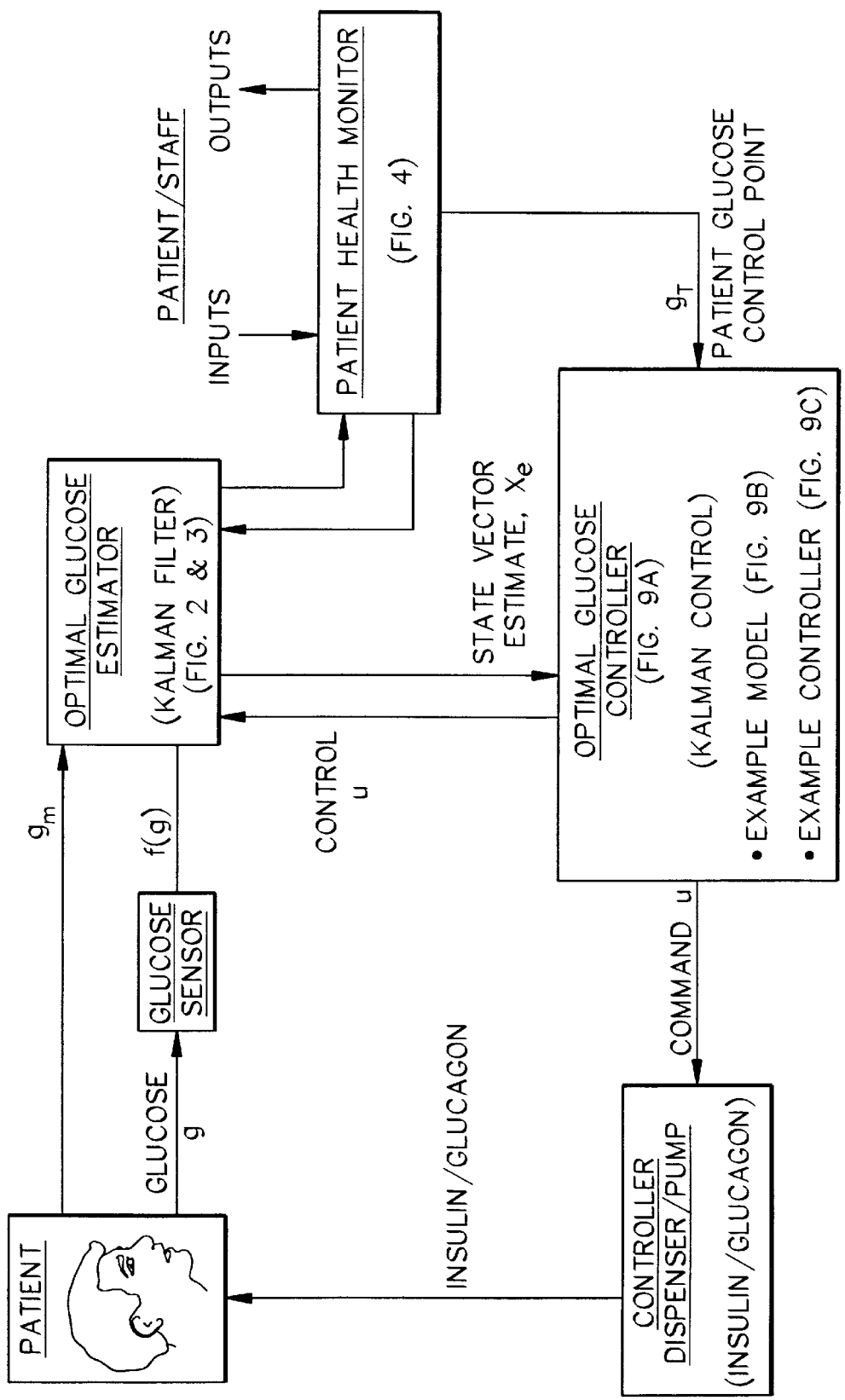
FIG. 8 is a functional diagram of one embodiment of an artificial pancreas.

FIG. 8 is a block diagram of one embodiment of a Kalman optimal stochastic control solution as applied to physiological processes. In one embodiment, the application includes both optimal stochastic regulator and optimal stochastic tracking control solutions. Tracking control involves a controlled variable following a reference value, constant or dynamic, as closely as possible. Control is applied to physiological processes, wherein a control gain is computed based upon optimization criteria which minimizes controlled variable errors while minimizing application of control based on cost weightings.

There is a duality between the computation of a Kalman estimator gain and a Kalman control gain. The Kalman estimator gain minimizes estimation error variances. The Kalman control gain minimizes variances of error between the controlled variables and the reference variables while minimizing the level of control applied. As a result, the optimal control function includes specification of the controlled variables and their associated costs as well as costs associated with the amount of control to be applied. For example, smaller control variable error costs and larger control application costs will allow the controlled variable to deviate farther from the reference, but with reduced application of control.

In one embodiment, linearization techniques described above in association with the Kalman estimator is applied to physiological nonlinear stochastic processes. For example, linearization about nominal values or about best estimates are provided by the Kalman estimator. Uncertain parameters associated with a controllable dispenser, or actuator, are included in an estimator state vector.

The optimal stochastic controller can use linear or nonlinear formulations and discrete or continuous time formulations. In one embodiment, the optimal stochastic controller is used with an optimal estimator described herein and/or an optimized decision and display function also described herein to form a closed loop system. The closed loop system works as an artificial pancreas when applied to a glucose problem-in one embodiment.

FIG. 8 is a functional diagram showing a controllable dispenser, or pump, with the capability to secrete insulin and glucagon to control high and low glucose levels, respectively. In one embodiment of a closed loop system, an estimator and a controller share a state vector wherein the estimator estimates it and the controller controls designated elements of it. Unlike the estimator, the time varying gain computations for the controller is computationally intensive and may not be used in all applications. The controller includes time varying or steady state gain formulations.

Figure 9A:
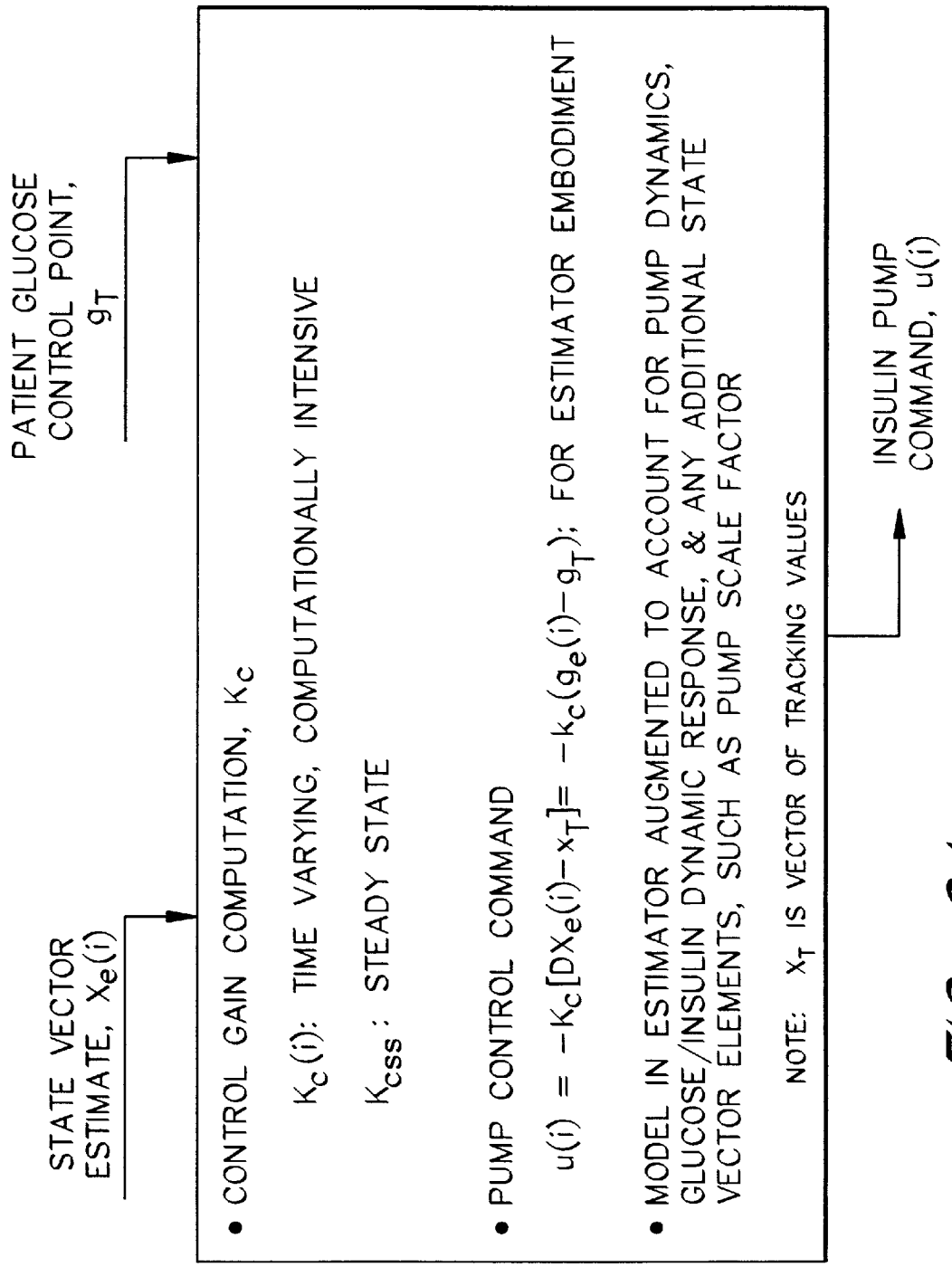
FIG. 9A illustrates one embodiment of an optimal controller for a closed loop system.

FIG. 9A illustrates one embodiment of an optimal controller for the artificial pancreas. The glucose control problem is a tracking problem since the glucose level is controlled to a desired level which may either be constant or a function of time. In one embodiment, the dynamic process model includes a quantitative description of how glucose levels propagate, in time, as a function of insulin/glucagon secreted by the controllable pump. The dynamic process model is described by a system of first order differential or difference equations. Excluding the pump, much of the modeling for the glucose control is available through the estimator modeling development.

FIG. 9B illustrates one embodiment of a control model for a controller. In an example embodiment, the dynamic process model is described by three first order differential equations that are forced by a control variable, u. The dynamics of this process include a first order time lag and a scale factor associated with the pump, and a first order time lag and a scale factor associated with the physiological process. The model for the glucose sensors is the same as in the example glucose estimator embodiment. In the definition of the elements of the transition matrix, alpha g, s, and d are the inverse of the first order time lags associated with glucose, glucose sensor scale factor, and pump, respectively. Beta g is the glucose scale factor multiplied by alpha g. Delta t is the time interval between measurement/control application epochs. The controlled error is the difference between the estimate of glucose (provided by the estimator) and the glucose control point input.

In a controller command, Beta d is a pump scale factor multiplied by alpha d. The measurements are the same as for the example glucose estimator, except that the measurements contain an additional zero since the measurements are not functions of the variable insulin/glucagon.

The cost function, which is minimized by the optimal stochastic control, contains costs associated with the glucose error and the application of control. Choosing a value of Cu that is much larger than Cg will result in a relative gentle application of control. Another example embodiment would utilize a higher order model in which the first derivative of glucose would be included in the state vector, and included as a control variable. If a relatively large cost is associated with the first derivative relative to the glucose control point error, then the control will be very active when rapid changes in patient glucose occur while relatively gentle otherwise. Other example embodiments would include pump scale factor as a state vector element (uncertain parameter) as well as insulin/glucagon measurements to the estimator.

FIG. 9C illustrates one embodiment of a control algorithm based on the model defined in FIG. 9B. Using either a time varying gain or a pre-computed steady state gain, control is applied at each epoch based upon a difference between an estimate of a patient glucose level and a glucose control point. A control, u, is applied to a pump over each time interval, and a state vector is time updated as indicated in this figure using the control variable, u, as a forcing function. Other time updates are performed in accordance with embodiments discussed above in association with estimator equations.

A potential problem in the application of closed loop control to that of physiological processes is due to potentially long time delays that may be de-stabilizing. These delays can be in the form of transport lags. A transport lag is the time between when control is applied and when the process action begins. An optimal technique for control using delay states is discussed in "Optimal Control of Linear Stochastic Systems with Process and Observation Time Delays" by E. J. Knobbe (Academic Press, Inc., 1989) and is hereby incorporated herein in its entirety by reference thereto. A discussion of principles developed for optimal control with process and observation time delays is provided in Table 5.

Although described above in connection with particular embodiments of the present invention, it should be understood that the descriptions of the embodiments are illustrative of the invention and are not intended to be limiting. Various modifications and applications may occur to those skilled in the art without departing from the true spirit and scope of the invention.

TABLE 1

SUMMARY OF CONTINUOUS-DISCRETE
EXTENDED KALMAN FILTER

| | |
|---|---|
| System Model | $\dot{\underline{x}}(t) = \underline{f}(\underline{x}(t), t) + \underline{w}(t); \quad \underline{w}(t) \sim N(\underline{0}, Q(t))$ |
| Measurement Model | $\underline{z}_k = \underline{h}_k(\underline{x}(t_k)) + \underline{v}_k; \quad k = 1, 2, \ldots; \quad \underline{v}_k \sim N(\underline{0}, R_k)$ |
| Initial Conditions | $\underline{x}(0) \sim N(\hat{\underline{x}}_o, P_o)$ |
| Other Assumptions | $E[\underline{w}(t)\underline{v}_k^T] = 0$ for all $k$ and all $t$ |

TABLE 1-continued

SUMMARY OF CONTINUOUS-DISCRETE
EXTENDED KALMAN FILTER

| | |
|---|---|
| State Estimate Propagation | $\dot{\hat{x}}(t) = \underline{f}(\hat{\underline{x}}(t), t)$ |
| Error Covariance Propagation | $\dot{P}(t) = F(\hat{\underline{x}}(t), t)P(t) + P(t)F^T(\hat{\underline{x}}(t), t) + Q(t)$ |
| State Estimate Update | $\hat{\underline{x}}_k(+) = \hat{\underline{x}}_k(-) + K_k[\underline{z}_k - \underline{h}_k(\hat{\underline{x}}_k(-))]$ |
| Error Covariance Update | $P_k(+) = [I - K_k H_k(\hat{\underline{x}}_k(-))]P_k(-)$ |
| Gain Matrix | $K_k = P_k(-)H_k^T(\hat{\underline{x}}_k(-))[H_k(\hat{\underline{x}}_k(-))P_k(-)H_k^T(\hat{\underline{x}}_k(-)) + R_k]^{-1}$ |
| Definitions | $F(\hat{\underline{x}}(t), t) = \left.\dfrac{\partial \underline{f}(\underline{x}(t), t)}{\partial \underline{x}(t)}\right|_{\underline{x}(t)=\hat{\underline{x}}(t)}$ |
| | $H_k(\hat{\underline{x}}_k(-)) = \left.\dfrac{\partial \underline{h}_k(\underline{x}(t_k))}{\partial \underline{x}(t_k)}\right|_{\underline{x}(t_k)=\hat{\underline{x}}_k(-)}$ |

TABLE 2

SUMMARY OF CONTINUOUS-DISCRETE
LINEARIZED KALMAN FILTER

| | |
|---|---|
| System Model | $\dot{\underline{x}}(t) = \underline{f}(\underline{x}(t), t) + \underline{w}(t); \quad \underline{w}(t) \sim N(\underline{0}, Q(t))$ |
| Measurement Model | $\underline{z}_k = \underline{h}_k(\underline{x}(t_k)) + \underline{v}_k; \quad k = 1, 2, \ldots; \quad \underline{v}_k \sim N(\underline{0}, R_k)$ |
| Initial Conditions | $\underline{x}(0) \sim N(\hat{\underline{x}}_o, P_o)$ |
| Other Assumptions | $E[\underline{w}(t)\underline{v}_k^T] = 0$ for all $k$ and all $t$ |
| | Nominal trajectory $\overline{x}(t)$ is available |
| State Estimate Propagation | $\dot{\hat{x}}(t) = \underline{f}(\overline{x}(t), t) + P(\overline{x}(t), t)[\overline{x}(t) - \overline{x}(t)]$ |
| Error Covariance Propagation | $\dot{P}(t) = F(\overline{x}(t), \tau)P(t) + P(t)F^T(\overline{x}(t), t) + Q(t)$ |
| State Estimate Update | $\hat{\underline{x}}_k(+) = \hat{\underline{x}}_k(-) + K_k[\underline{z}_k - \underline{h}_k(\overline{x}(t_k))[\hat{\underline{x}}_k(-) - \overline{x}(t_k)]]$ |
| Error Covariance Update | $P_k(+) = [I - K_k H_k(\overline{x}(t_k))]P_k(-)$ |
| Gain Matrix | $K_k = P_k(-)H_k^T(\overline{x}(t_k))[H_k(\overline{x}(t_k))P_k(-)H_k^T(\overline{x}(t_k)) + R_k]^{-1}$ |
| Definitions | $F(\hat{\underline{x}}(t), t) = \left.\dfrac{\partial \underline{f}(\underline{x}(t), t)}{\partial \underline{x}(t)}\right|_{\underline{x}(t)=\hat{\underline{x}}(t)}$ |
| | $H_k(\hat{\underline{x}}_k(t_k)) = \left.\dfrac{\partial \underline{h}_k(\underline{x}(t_k))}{\partial \underline{x}(t_k)}\right|_{\underline{x}(t_k)=\hat{\underline{x}}_k(-)}$ |

TABLE 3

State Vector

X, Xe, Xe(0): These symbols denote, respectively, the state vector, the best estimate (or optimal estimate) of the state vector, and the initial best estimate of the state vector. They contain both variables and parameters as defined above and, with regard to estimation, there are no distinctions.
Dynamic Process Model dX = f(X,t), dXe = f(Xe,t): These symbols denote the time derivative of the state vector and estimated state vector, respectively. They represent a system of first order differential equations (or difference equations) which describe the manner in which the state elements propagate in time. The function, f, may be linear or nonlinear.
Measurement Model Ym = h(X) + e, Ye = h(Xe): These symbols denote the actual measurement and the best estimate of the measurement, respectively. The function, h, defines the arbitrary, but known, way in which the state vector elements are related to the measurement, and e represents the sensor measurement error.
Covariance Matrix P, P(0): Denotes, respectively, the matrix of variances and co-variances associated with the errors of each of the state variable estimates (within the estimated state vector) and their initial values,
Transition Matrix A, A(0): Denotes the transition matrix, which is used to propagate the covariance matrix forward it time (time update), and it's initial value, respectively; in the linear case it is also used to time update the state
vector estimate.
Process Noise Matrix Q: Denotes the matrix of variances and co-variances associated with error growth uncertainty accumulated in the state variable estimates since the last measurement update,
Measurement Matrix H, H(0): Denotes the measurement matrix and it's initial value, respectively. This matrix defines the linear functional relationship between the measurement and the state vector elements. If, the measurement model is linear, then H = h, if h is non-linear, then H is defined by linearizing h using partial derivatives
or perturbation techniques.
Measurement Noise Matrix R: Denotes the matrix of variances and co-variances associated with measurement error uncertainties.
Kalman Gain Matrix K: Denotes the Kalman gain matrix which, when multiplied by the difference between the actual measurement, and the best estimate of the measurement, yields the estimated state correction. This estimated state correction, when added to the old best estimate, becomes the new best estimate.
Estimated Measurement Error (Residual)

y = Ym-Ye: Denotes the difference between the actual measurement and the best estimate of the measurement. This difference multiplied by the Kalman gain yields the correction to the previous state vector estimate.

TABLE 4

% Optimal Glucose Estimator, Extended Kalman Filter; Computes
Statistical Test Data for
Patient Health Monitor
%Ed_JYP_Estimator; Two-step scale-factor model,
Exp = .999 for t>20; r=15^2 for y<10;
x=[150;.25]; hh=[10];p=[100^20; 0.1^2];a=[10; 01];
q=[20^20; 0.002^2]; rr= 15^2;
r=5^2; I=[10;01];
load EdJY528.prn,
[m,n]=size(EdJY528),

TABLE 4-continued

```
t=EdJY528(:,1)/12;
y=EdJY52B(:,2);
g=EdJY528(:,3);
gm=EdJY528(:,4);
x=[gm(1); .25];
sz=0.0;
SVZ = p(1,1)*x(2)^2 + p(2,2)*x(1)^2;
for i = 1:m;...
    r = 5^2;...
    zz = 0;...
    if y(i) < 10
        r = 15^2;...
    end;
    if t(i) > 20    a=[10; 0.9991;...
    end;
    p=a*p*a'+q;...
    x=a*x;...
    if gm(i) > 0
        k=p*hh'/(hh*p*hh'+rr);...
        zz=(gm(i)-x(1));...
        x=x+k*zz;...
        p=(I-k*hh)*p;...
    end;
    h=[x(2) x(1)];...
    k=p*h'/(h*p*h'+r);...
    z=(y(i)-x(1)*x(2));...
    x=x+k*z;...
    p=(I-k*h)*p;...
    az=abs(z);...
    sz=sz+z;...
    asz = abs(sz);...
    VZ = p(1,1)*x(2)^2 + p(2,2)*x(1)^2 + 2*p(1,2)*x(1)*x(2)+r;...
    sigZ = sqrt(Vz);...
    SVZ = SVZ + VZ;...
    sigSZ = sqrt(SVZ);...
    VZZ = p(1,1) + rr;...
    sigZZ = sqrt(VZZ);...
    azz = abs(zz);...
    xhistory(i,1) = x(1);...
    xhistory(i,2) = x(2);...
    gmhistory =gm;..
    ghistory =g;...
    zhistory(i) =z;...
    sigsz_history(i) = sigSZ;...
    sigz_history(i) = 2*sigZ;...
    aszhistory(i) = asz;...
    azhistory(i) = az;...
    zzhistory(i) = zz;...
    sigzz_history(i) = 2*sigZZ;...
    azzhistory(i) = azz;...
    sig_history(i,1)=sqrt(p(1,1));...
    sig_history(i,2)=sqrt(p(2,2));...
    yhistory=y;...
end;
figure (1)
plot(t,xhistory(:,2));
xlabel('Measurement Time (hrs)');
ylabel('Scale Factor Estimate; (ISIG Units/(mg/dl))');
title('Scale Factor Estimate vs Time');
figure (2)
plot(t,gmhistory(:),t,xhistory(:,1));
xlabel ('Time (hrs)');
Ylabel('Glucose Meas & Estimated Glucose; (mg/dl)');
title('All Glucose Measurements & Estimated Glucose vs Time');
figure (3)
plot(t, yhistory(:), t,zhistory (:));
xlabel('Time (hrs)');
Ylabel('ISIG Meas & z Residual; (ISIG Units)');
title('ISIG Measurement & z residual vs Time');
figure (4)
plot(t,xhistory(:,1),t,ghistory(:,1));
xlabel('Time (hrs)');
ylabel('Glucose & Estimated Glucose; (mg/dl)');
title('Glucose Estimate & All Glucose CBGs vs Time');
figure (5)
plot(t,sigzz_history(:),t,azzhistory(:));
xlabel('Time (hrs)');
ylabel('Abs(zz) Residual & two sigma(zz); (mg/dl)');
title('Residual Test: 2 Sigma(zz) & Abs(zz) Residual vs Time');
```

TABLE 4-continued figure (6)
plot(t,azhistory(:),t,sigz_history(:));
xlabel('Measurement Time (hrs)');
ylabel('z Residual & Standard Deviation; (ISIG Units)');
title('Residual Test: Abs(z) & 2 Sigma(z) vs Time');
figure (7)
plot(t,aszhistory(:),t,sigsz_history(:));
xlabel('Measurement Time (hrs)');
ylabel('sz Residual & Sigma; (ISIG Units)');
title('Residual Test: Abs(sz) & Sigma(sz) vs Time');

TABLE 5

PROBLEM DEFINITION

The general, discrete-time system representation with explicit process and observation time delays is given by $$x(k+1) = \sum_{i=1}^{q} A_i(k)X(k+1-i) + B(k)U(k) + W_1(k), \quad (1)$$

$$Y(k) = \sum_{j=1}^{p} C_j(k)X(k+1-j) + W_k(k), \quad (2)$$

where p and q are integers>1; $W_1$ and $W_2$ are zero-mean white-noise sequences such that $$\left. \begin{array}{l} E\{W_1(k)W_1^T(k)\} = V_1(k) \\ E\{W_2(k)W_2^T(k)\} = V_2(k) \\ E\{W_1(i)W_2^T(j)\} = 0 \end{array} \right\} \forall_{i,j,k};$$

Y is an m×1 observation vector; X is an n×1 random state vector whose initial uncertainty is uncorrelated with $W_1$ and $W_2$ and with initial covariance $Q_0$; and U is the control input vector. The objective is to find the control function (functional) U(k) for k=1,2, ... that minimizes an expected quadratic cost function for the linear stochastic regulator defined by Eqs. (1) and (2). Because linear stochastic tracking problems can be formulated as linear stochastic regulator problems by combining the reference and plant models in an augmented system [3], this system representation applies equally to the tracking problem.

Problem Formulation and Solution

The system representation defined by Eqs. (1) and (2) can be cast in stochastic regulator form by augmenting the state vector with the time-delayed states, that is, $$\overline{X}(k+1) = \overline{A}(k)\overline{X}(k) + \overline{B}(k)U(k) + \overline{W}_1(k), \quad (3)$$

and $$Y(k) = \overline{C}(k)\overline{X}(k) + W_2(k) \quad (4)$$

$$\overline{A}(k) \triangleq \begin{bmatrix} 0 & I & 0 & \cdots & 0 \\ & 0 & \ddots & & \\ \vdots & & \ddots & & \vdots \\ & & & \ddots & 0 \\ 0 & & \cdots & 0 & I \\ A_h(k) & & \cdots & & A_1(k) \end{bmatrix}, \quad \overline{X}(k) \triangleq \begin{bmatrix} X(k-h+1) \\ X(k-h+2) \\ \vdots \\ X(k-1) \\ X(k) \end{bmatrix},$$

$$\overline{B}(k) \triangleq \begin{bmatrix} 0 \\ \vdots \\ 0 \\ B(k) \end{bmatrix}, \quad \overline{W}(k) \triangleq \begin{bmatrix} 0 \\ \vdots \\ 0 \\ W_1(k) \end{bmatrix}, \quad \overline{C}(k)^T \triangleq \begin{bmatrix} C_h(k) \\ C_{h-1}(k) \\ \vdots \\ C_2(k) \\ C_1(k) \end{bmatrix}$$

and the dimensionality of the system is defined by h, where h=max(p,q).

In Eq. (3), the control remains the same as in Eq. (1) because, physically, past states cannot be changed or controlled. In Eq. (4) the observation Y and the observation noise $W_2$ also remain unchanged.

In Eqs. (1) and (2), p and q are not, in general, equal. For example, if the observation is not a linear function of all the delayed states contained in $\overline{X}$, then h=q>p, and the appropriate (q−p) submatrices in $\overline{C}$, of Eq. (4), are set equal to zero. If the process evolution is not a linear function of all the delayed states contained in $\overline{X}$, then h=p>q, and the appropriate submatrices in $\overline{A}$, of Eq. (3) are set equal to zero. The dimensions of $\overline{B}$ and $\overline{W}_1$, in Eq. (3), must also be consistent with the integer h. Therefore, without loss of generality, the system defined by Eqs. (1) and (2) can be represented by the augmented system model described by Eqs. (3) and (4).

Given that the control is to minimize the expected value of a quadratic cost function of the form, $$E\left\{ \sum_{k=k_0}^{k_1-1} \left[ \overline{X}(k)^T \overline{R}_1(k) \overline{X}(k) + U^T(k) R_2(k) U(k) \right] + \overline{X}(k_1) \overline{P}(k_1) \overline{X}(k_1) \right\}, \quad (5)$$

then the separation principle applies [3]. Also, the optimal linear stochastic control of the augmented system is given by a deterministic, optimal linear controller with state input $\overline{X}$ (or estimated state feedback), which is provided by an optimal one-step predictor, using the augmented model [4]. That is, $$U(k) = -\overline{F}(k)\hat{\overline{X}}(k); \quad k=k_0, k_0+1, \ldots, k_1 \quad (6)$$

where the control gain $\overline{F}$ satisfies $$\overline{F}(k) = \{R_2(k) + \overline{B}^T(k)[\overline{R}_1(k+1) + \overline{P}(k+1)]\overline{B}(k)\}^{-1} \quad (7)$$

$$\overline{B}^T(k)[\overline{R}(k+1) + \overline{P}(k+1)]\overline{A}(k);$$

the matrix $\overline{P}$ satisfies the recursive matrix Riccati equation, $$\overline{P}(k) = \overline{A}^T(k)[\overline{R}_1(k+1) + \overline{P}(k+1)][\overline{A}(k) - \overline{B}(k)\overline{F}(k)]; \quad (8)$$

the one-step predictor output $\hat{\overline{X}}$ is defined by $$\hat{\overline{X}}(k+1) = \overline{A}(k)\hat{\overline{X}}(k) + \overline{B}(k)U(k) + \overline{K}(k)[Y(k) - \overline{C}(k)\hat{\overline{X}}(k)]; \quad (9)$$

the estimator gain $\overline{K}$ satisfies $$\overline{K}(k) = \overline{A}(k)\overline{Q}(k)\overline{C}^T(k)[\overline{C}(k)\overline{Q}(k)\overline{C}^T(k) + V_2(k)]^{-1}; \quad (10)$$

and the state estimation error covariance matrix $\overline{Q}$ satisfies the recursive matrix Riccati equation, $$\overline{Q}(k+1) = [\overline{A}(k) - \overline{K}(k)\overline{C}(k)]\overline{Q}(k)\overline{A}^T(k) + V_1(k). \quad (11)$$

The final value of $\overline{P}$ used to "initialize" Eq. (8) (which is solved backward in time) is the final value defined in the quadratic cost function of Eq. (5), that is, $\overline{P}(k_1) = \overline{P}_1$. The initial value of $\bar{Q}$ used to initialize Eq. (11) is the error covariance of the initial estimate of X, that is, $\bar{Q}(0)=\bar{Q}_0$.

If the system statistics defined in Eqs. (1) and (2) are gaussian, then the above solution is the optimal solution without qualification; if not, then it is the optimal linear control solution. The expected system performance is determined by analyzing the augmented system as a linear, stochastic regulator problem.

Practical Applications

From control gain Eqs. (7) and (8) and estimator pain Eqs. (10) and (11), it can be shown that the required dimensions of the controller and estimator are not, in general, equal. The dimensions of the control matrix Riccati equation (8) is determined by the number of delayed stales in the process evolution, that is, $\bar{P}$ has the dimensions of n·q×n·q. Consequently, for the special case of measurement delays only (q=1), the controller implementation is unaffected. However, the dimensions of the estimator matrix Riccati equation (11) are determined by the maximum of p and q. Since h=max(p,q) then Q has the dimensions n·h×n·h. For the general case, the optimal control is given by $$U(k) = -\sum_{i=1}^{q} F_i(k)\hat{X}(k+1-i), \quad (12)$$

where $$\bar{F}(k) \triangleq [F_q(k)F_{q-1}(k) \ldots F_2(k)F_1(k)], \quad (13)$$

and $$\hat{X}^T(k) \triangleq [\hat{X}^T(k+1-h) \ldots \hat{X}^T(k+1-q) \ldots \hat{X}(k-1)\hat{X}^T(k)]. \quad (14)$$

We note that, in Eq. (14), $\hat{X}(k)$ is the one-step predicted value of the original system state vector; $\hat{X}(k-1)$ is the filtered value; $\hat{X}(k-2)$ is the one-step smoothed value; and, finally, $\hat{X}(k+1-h)$ is the (h-2)th smoothed value.

Typically, the real-time computational requirements associated with the implementation of time-varying optimal control are always stressing due to the "backward-in-time" recursion that is required to obtain solutions $\bar{P}$ of Eq. (8). However, in many high-accuracy applications, the $\bar{A}$, $\bar{B}$, $\bar{R}_1$, and $R_2$ matrices of the augmented system and cost function can be treated as time invariant over the time intervals of interest. Further, if the augmented system satisfies the relatively minor requirements of stabilizability and detectability, then the control gain $\bar{F}$ will converge to a unique value such that the steady-state optimal control law is time invariant, asymptotically stable, and minimizes the quadratic cost function of Eq. (5) as $k_1 \to \infty$. For this case, the steady-state gain matrix $\bar{F}_{ss}$ can be computed off-line and stored for real-time use; the real-time computations required to implement this steady-state control law are negligible.

Usually, for (racking and regulator problems, the steady-state control gains and time-varying gains are such that the initial value of the time-varying gain is equal to the steady-state gain but is less than or equal to the steady-state gain as time progresses, that is, $\bar{F}_{ss} \geq \bar{F}(k)$ for $k_0 \leq k \leq k_1$.

As a consequence, the steady-state gain tends to maintain the controlled state closer to the estimated state, but at the cost of control energy. If accuracy is the significant criterion, then the steady-state gain is not only easy to implement but also provides essentially equivalent or better accuracy.

This, however, is not the case for the estimator gain, even though in most cases where linear steady-state optimal stochastic control is implemented, both the steady-state control and the estimator gains are used. For the estimator and the same general conditions as before, the initial time-varying estimator gain is usually significantly larger than the steady-state gain, to account for initial uncertainties in the knowledge of the system state. As time progresses, the time-varying gain converges to the steady-state gain, that is, $\bar{K}_{ss} \leq \bar{K}(k)$ for $k_0 \leq k \leq k_1$.

Consequently, initial system performance is significantly degraded if $K_{ss}$ is used. In fact, if applied to a "linearized" system, the estimator can actually diverge given the initial small steady-state filter gains.

Hence a good compromise between performance and computational complexity is to choose the steady-state controller with the time-varying estimator. Further, because the estimator matrix Riccati equation is solved forward in time, the computations associated with the time-varying filter gain are orders of magnitude less than with the time-varying control gain and can usually be implemented in real time.

Although the computations associated with the augmented system estimator are significantly increased because of the increased dimensions, some simplifications can be made. The estimator Riccati equation can be separated into a time update and a measurement update, where the time update for the augmented system becomes primarily one of data transfer. If $\bar{Q}$, from Eq. (11), is defined as $$Q(k) = \begin{bmatrix} Q_{1,1}(k) & Q_{1,2}(k) & \cdots & Q_{1,h}(k) \\ Q_{2,1}(k) & Q_{2,2}(k) & \cdots & \vdots \\ \vdots & & \ddots & \\ Q_{h,1}(k) & \cdots & & Q_{h,h}(k) \end{bmatrix}, \quad (15)$$

then, for the special case where q=1 and p≥2, the time update becomes $$\begin{aligned} Q_{i,j}(k+1) &= Q_{i+1,j+1}(k) \\ Q_{i,p}(k+1) &= Q_{i+1,p}(k)A_1^T(k) \\ Q_{p,p}(k+1) &= A_1(k)Q_{p,p}(k)A_1^T(k) + V_1(k) \end{aligned} \bigg\} \; i,j=1,\ldots,p-1 \bigg\}. \quad (16)$$

For the worst case, where q>p>1, the time update is given by $$\begin{aligned} Q_{i,j}(k+1) &= Q_{i+1,j+1}(k), \quad i,j=1,\ldots,q-1, \\ Q_{i,q}(k+1) &= \sum_{j=1}^{q} Q_{i,j}(k)A_{(q+1)-j}^T(k), \quad i=1,\ldots,q-1, \\ Q_{q,q}(k+1) &= \sum_{i=1}^{q}\sum_{j=1}^{q} A_{(q+1)-i}(k)Q_{i,j}(k)A_{(q+1)-j}^T(k) + V_1(k) \end{aligned} \bigg\}. \quad (17)$$

In practice, another computational simplification results because rarely, if ever, is the actual system measurement a function of every time-delayed state element, and likewise for the actual system process model. Hence the submatrices $A_i$ and $C_i$ (for i>1) in $\bar{A}$ and $\bar{C}$, respectively, are usually of significantly reduced dimension. This, in turn, significantly reduces the dimensions of the augmented system model.

We note that the iteration interval $\Delta t$ (implied in the discrete-time system representation) or some integer number of $\Delta t$'s should be set equal to the time delay. For variable time delays, it may be advantageous to use (a) variable iteration intervals for the estimator. (b) fixed iteration intervals for the controller, and (c) variable-time updates of the state estimate to time synch the estimator output with the controller input.

Finally, for the analogous continuous-time problem, the filter equation becomes a partial differential equation with a boundary condition, and the covariance equation becomes a partial differential matrix equation with three boundary conditions (see [2]). Consequently, the most practical control solution is obtained by discretizing the continuous-time system representation and then applying the approach of Section III. One technique for discretizing the continuous-time representation is by using the Z transform method; see, for example, [5]. Using a scalar differential equation with one delayed state as an example, we have $$\dot{X}(t) = \sum_{i=0}^{1} a_i X(t - i\Delta t) + U(t). \tag{18}$$

If assume that the output solution X(t) is sampled in discrete time, and if the system process can be reasonably approximated by a continuous system in which X is driven by the output of a high-frequency sampling of the right side of Eq. (18), then the discrete-time process model is given by $$X(k+1) = (1 + a_0 \Delta t) X(k) + (a_1 \Delta t) X(k - \Delta t) + (\Delta t) U(k). \tag{19}$$

The approximate discrete-time solution to Eq. (18), which is given by Eq. (19) is now in a form consistent with Eq. (1) of Section II, and the approach of Section III can be applied.

What is claimed is:

1. A method for providing a best estimate of glucose level in real time comprising the acts of:
    obtaining a measurement which is a function of glucose level, wherein noise associated with the measurement is within limits of a predefined measurement uncertainty;
    supplying the measurement to an extended Kalman filter in real time, wherein the extended Kalman filter has a dynamic process model, a dynamic measurement model, a state vector with at least one element corresponding to glucose level, and an error covariance matrix of the state vector; and
    determining the best estimate of glucose level in real time using the extended Kalman filter.

2. The method of claim 1, wherein the extended Kalman filter is implemented using a software algorithm.

3. The method of claim 1, wherein determination of the best estimate of glucose level in real time uses a recursive process comprising the acts of:
    computing a current estimate of the state vector using a preceding best estimate of the state vector and the dynamic process model;
    computing a current error covariance matrix of the state vector using a preceding error covariance matrix of the state vector, uncertainties associated with the dynamic process model, and the dynamic process model linearized about the current estimate of the state vector;
    computing a Kalman gain using the current covariance matrix, uncertainties associated with the dynamic measurement model, and the dynamic measurement model linearized about the current estimate of the state vector;
    computing a new error covariance matrix of the state vector using the current error covariance matrix of the state vector, the Kalman gain, and the dynamic measurement model linearized about the current estimate of the state vector; and
    computing a new best estimate of the state vector using the current estimate of the state vector, the Kalman gain, the measurement, and the dynamic measurement model.

4. The method of claim 1, wherein development of the dynamic process model and the dynamic measurement model is an iterative process comprising the acts of:
    defining estimation variables and uncertain parameters which become elements of the state vector;
    defining nominal time propagation of the estimation variables and the uncertain parameters;
    defining a nominal sensor measurement model;
    defining relationships between the estimation variables, the uncertain parameters, and the measurement;
    defining uncertainties associated with the estimation variables, the uncertain parameters, and the measurement; and
    verifying a nominal dynamic process model and a nominal measurement model.

5. The method of claim 4, wherein a database of measurements is used to empirically verify the nominal dynamic process model and the nominal measurement model.

6. The method of claim 5, wherein the database has a plurality of sensor measurements with corresponding direct measurements.

7. A real-time glucose estimator comprising:
    a plurality of measurement inputs, wherein at least one of the measurement inputs is configured to receive an input indicative of glucose level;
    a plurality of control inputs; and
    an extended Kalman filter algorithm configured to receive the plurality of measurement inputs and the plurality of control inputs to provide an optimal estimate of glucose level in real time.

8. The real-time glucose estimator of claim 7, wherein at least two independent glucose sensors are coupled to the measurement inputs respectively.

9. The real-time glucose estimator of claim 8, wherein at least two independent glucose sensors are of different types.

10. The real-time glucose estimator of claim 7, wherein at least one of the measurement inputs is configured to receive a direct measurement of glucose.

11. The real-time glucose estimator of claim 10, wherein the direct measurement is derived from a capillary blood glucose measurement.

12. The real-time glucose estimator of claim 7, wherein at least one of the control inputs is configured to receive configuration data.

13. The real-time glucose estimator of claim 7, wherein at least one of the control inputs is configured to receive environment data.

14. The real-time glucose estimator of claim 7, wherein the extended Kalman filter algorithm produces the optimal estimate of glucose level in real time using a recursive loop formed by a time update module and a measurement update module.

15. The real-time glucose estimator of claim 14, wherein the plurality of control inputs is processed in real time by the time update module.

16. The real-time glucose estimator of claim 14, wherein the plurality of measurement inputs is processed in real time by the measurement update module.

17. The real-time glucose estimator of claim 16, wherein measurement inputs of a substantially identical time interval are processed serially in one cycle of the measurement update module.

18. The real-time glucose estimator of claim 10, wherein the direct measurement is provided during initialization of the real-time glucose estimator and intermittently thereafter.

19. The real-time glucose estimator of claim 7, wherein at least one of the measurement inputs is provided periodically to the real-time glucose estimator.

20. The real-time glucose estimator of claim 7, wherein at least one of the measurement inputs is coupled to a non-invasive glucose sensor.

21. The real-time glucose estimator of claim 7 further comprising a patient health monitor configured to accept user inputs, to derive configuration data based on the user inputs, and to provide the configuration data in real time to the real-time glucose estimator.

22. The real-time glucose estimator of claim 7 further comprising a patient health monitor configured to display in real time the optimal estimate of glucose level and to provide an audible alarm when the optimal estimate of glucose level is outside a predetermined range.

23. The real-time glucose estimator of claim 10 further comprising a patient health monitor configured to display in real time a performance status for the real-time glucose estimator, wherein the performance status is based upon results of statistical testing performed on residuals of the extended Kalman filter.

24. The real-time glucose estimator of claim 23, wherein the patient health monitor outputs a request for the direct measurement of glucose when the performance status indicates the optimal estimate of glucose level is outside predetermined limits.

25. An estimator for monitoring a physiological parameter comprising:
   a sensor which outputs a measurement as a function of the physiological parameter;
   an electronic processor coupled to an output of the sensor, wherein the electronic processor executes an algorithm that implements an extended Kalman filter to estimate the physiological parameter in real time; and
   an interface coupled to an output of the electronic processor to display the estimate of the physiological parameter in real time.

26. The estimator of claim 25, wherein the interface accepts user inputs and provides a control signal in real time to the electronic processor based on the user inputs.

27. The estimator of claim 26, wherein the user inputs describe environmental conditions of the sensor in real time.

28. The estimator of claim 26, wherein the user inputs describe activities of a patient using the estimator in real time.

29. The estimator of claim 26, wherein the user inputs describe real-time administration of medication to a patient using the estimator.

30. The estimator of claim 25, wherein the estimator is a portable device contained in a relatively small package and battery operated.

31. An estimator comprising:
   means for obtaining a measurement related to a physiological parameter; and
   means for processing the measurement in real time using a linearized Kalman filter algorithm to provide a real-time estimate of the physiological parameter.

32. The estimator of claim 31 further comprising means for displaying the real-time estimate of the physiological parameter in real time.

33. The estimator of claim 31 further comprising means for updating the linearized Kalman filter algorithm in real time with user inputs.

34. The estimator of claim 31 further comprising means for indicating performance status of the estimator in real time.

* * * * *